US007147673B2

(12) United States Patent
Plos et al.

(10) Patent No.: US 7,147,673 B2
(45) Date of Patent: Dec. 12, 2006

(54) COMPOSITION FOR DYEING HUMAN KERATIN MATERIALS, COMPRISING AT LEAST ONE FLUORESCENT DYE AND AT LEAST ONE INSOLUBLE POLYORGANOSILOXANE CONDITIONING POLYMER, PROCESS THEREFOR AND USE THEREOF

(75) Inventors: Grégory Plos, Paris (FR); Henri Samain, Bievres (FR)

(73) Assignee: L'Oreal S.A., Paris (FR)

( * ) Notice: Subject to any disclaimer, the term of this patent is extended or adjusted under 35 U.S.C. 154(b) by 299 days.

(21) Appl. No.: 10/814,334

(22) Filed: Apr. 1, 2004

(65) Prior Publication Data

US 2005/0005369 A1 Jan. 13, 2005

Related U.S. Application Data

(60) Provisional application No. 60/468,079, filed on May 6, 2003.

(30) Foreign Application Priority Data

Apr. 1, 2003 (FR) .................................. 03 04033

(51) Int. Cl.
*A61K 7/13* (2006.01)
(52) U.S. Cl. ...................... 8/405; 8/406; 8/407; 8/410; 8/411; 8/421; 8/521; 8/581; 8/632; 8/648; 132/208
(58) Field of Classification Search ................... 8/405, 8/406, 407, 410, 411, 421, 521, 581, 632, 8/648; 132/208
See application file for complete search history.

(56) References Cited

U.S. PATENT DOCUMENTS

| | | | |
|---|---|---|---|
| 2,261,002 A | 10/1941 | Ritter | |
| 2,271,378 A | 1/1942 | Searle | |
| 2,273,780 A | 2/1942 | Ditmar | |
| 2,375,853 A | 5/1945 | Kirby et al. | |
| 2,388,614 A | 11/1945 | Kirby et al. | |
| 2,454,547 A | 11/1948 | Bock et al. | |
| 2,798,053 A | 7/1957 | Brown | |
| 2,851,424 A | 9/1958 | Switzer et al. | |
| 2,923,692 A | 2/1960 | Ackerman et al. | |
| 2,961,347 A | 11/1960 | Floyd | |
| 2,979,465 A | 4/1961 | Parran et al. | |
| 3,014,041 A | 12/1961 | Hausermann et al. | |
| 3,206,462 A | 9/1965 | McCarty | |
| 3,227,615 A | 1/1966 | Korden | |
| 3,472,840 A | 10/1969 | Stone et al. | |
| 3,632,559 A | 1/1972 | Matter et al. | |
| 3,639,127 A | 2/1972 | Brooker et al. | |
| 3,658,985 A | 4/1972 | Olson, Jr. et al. | |
| 3,856,550 A | 12/1974 | Bens et al. | |
| 3,874,870 A | 4/1975 | Green et al. | |
| 3,910,862 A | 10/1975 | Barabas et al. | |
| 3,912,808 A | 10/1975 | Sokol | |
| 3,915,921 A | 10/1975 | Schlatzer, Jr. | |
| 3,917,817 A | 11/1975 | Vanlerberghe et al. | |
| 3,929,990 A | 12/1975 | Green et al. | |
| 3,966,904 A | 6/1976 | Green et al. | |
| 3,986,825 A | 10/1976 | Sokol | |
| 4,001,432 A | 1/1977 | Green et al. | |
| 4,005,193 A | 1/1977 | Green et al. | |
| 4,013,787 A | 3/1977 | Vanlerberghe et al. | |
| 4,025,617 A | 5/1977 | Green et al. | |
| 4,025,627 A | 5/1977 | Green et al. | |
| 4,025,653 A | 5/1977 | Green et al. | |
| 4,026,945 A | 5/1977 | Green et al. | |
| 4,027,020 A | 5/1977 | Green et al. | |
| 4,031,307 A | 6/1977 | DeMartino et al. | |
| 4,075,136 A | 2/1978 | Schaper | |
| 4,131,576 A | 12/1978 | Iovine et al. | |
| 4,157,388 A | 6/1979 | Christiansen | |
| 4,165,367 A | 8/1979 | Chakrabarti | |
| 4,166,894 A | 9/1979 | Schaper | |
| 4,172,887 A | 10/1979 | Vanlerberghe et al. | |
| 4,185,087 A | 1/1980 | Morlino | |
| 4,189,468 A | 2/1980 | Vanlerberghe et al. | |
| 4,197,865 A | 4/1980 | Jacquet et al. | |
| 4,217,914 A | 8/1980 | Jacquet et al. | |
| 4,223,009 A | 9/1980 | Chakrabarti | |
| 4,237,243 A | 12/1980 | Quack et al. | |
| 4,240,450 A | 12/1980 | Grollier et al. | |
| 4,256,458 A | 3/1981 | Degen et al. | |
| 4,277,581 A | 7/1981 | Vanlerberghe et al. | |

(Continued)

FOREIGN PATENT DOCUMENTS

AT 302 534 10/1972

(Continued)

OTHER PUBLICATIONS

CAS Abstract for JP 2000-136340—Chemical Abstracts Service; Database Accession No. 2000: 317079; XP-002269220, JP 2000136340 (Pentel Co., Ltd.), May 16, 2000.

(Continued)

*Primary Examiner*—Eisa Elhilo
(74) *Attorney, Agent, or Firm*—Finnegan, Henderson, Farabow, Garrett & Dunner LLP

(57) ABSTRACT

Disclosed herein is a composition comprising at least one fluorescent dye and at least one insoluble polyorganosiloxane conditioning polymer, processes using this composition, and a device.

Further disclosed herein is the use of compositions comprising at least one fluorescent dye and at least one insoluble polyorganosiloxane conditioning polymer, for dyeing human keratin materials, for example artificially dyed and/or pigmented hair and dark skin, with a tightening effect.

52 Claims, No Drawings

U.S. PATENT DOCUMENTS

| | | | |
|---|---|---|---|
| 4,381,919 A | 5/1983 | Jacquet et al. | |
| 4,422,853 A | 12/1983 | Jacquet et al. | |
| 4,445,521 A | 5/1984 | Grollier et al. | |
| 4,509,949 A | 4/1985 | Huang et al. | |
| 4,591,610 A | 5/1986 | Grollier | |
| 4,608,250 A | 8/1986 | Jacquet et al. | |
| 4,693,935 A | 9/1987 | Mazurek | |
| 4,702,906 A | 10/1987 | Jacquet et al. | |
| 4,719,099 A | 1/1988 | Grollier et al. | |
| 4,719,282 A | 1/1988 | Nadolsky et al. | |
| 4,728,571 A | 3/1988 | Clemens et al. | |
| 4,761,273 A | 8/1988 | Grollier et al. | |
| 4,781,724 A | 11/1988 | Wajaroff et al. | |
| 4,823,985 A | 4/1989 | Grollier et al. | |
| 4,839,166 A | 6/1989 | Grollier et al. | |
| 4,948,579 A | 8/1990 | Jacquet et al. | |
| 4,961,925 A | 10/1990 | Tsujino et al. | |
| 4,972,037 A | 11/1990 | Garbe et al. | |
| 4,996,059 A | 2/1991 | Grollier et al. | |
| 5,009,880 A | 4/1991 | Grollier et al. | |
| 5,057,311 A | 10/1991 | Hanazawa et al. | |
| 5,089,252 A | 2/1992 | Grollier et al. | |
| 5,139,037 A | 8/1992 | Grollier et al. | |
| 5,188,639 A | 2/1993 | Schultz et al. | |
| 5,196,189 A | 3/1993 | Jacquet et al. | |
| 5,275,808 A | 1/1994 | De Groot et al. | |
| 5,356,438 A | 10/1994 | Kim et al. | |
| 5,445,655 A | 8/1995 | Kuhn et al. | |
| 5,635,461 A | 6/1997 | Onitsuka et al. | |
| 5,708,151 A | 1/1998 | Möckli | |
| 5,733,343 A | 3/1998 | Mockli | |
| 5,744,127 A * | 4/1998 | Giuseppe et al. | 424/59 |
| 5,792,221 A | 8/1998 | Lagrange et al. | |
| 5,830,446 A | 11/1998 | Berthiaume et al. | 424/70.1 |
| 5,833,997 A | 11/1998 | Mahieu et al. | |
| 5,853,708 A * | 12/1998 | Cauwet et al. | 424/70.22 |
| 5,873,494 A | 2/1999 | Dallas, Jr. | |
| 5,958,392 A | 9/1999 | Grollier et al. | |
| 5,962,522 A | 10/1999 | Wacher et al. | |
| 6,106,577 A | 8/2000 | Audousset et al. | |
| 6,120,780 A | 9/2000 | Dupuis et al. | |
| 6,180,666 B1 | 1/2001 | Wacher et al. | |
| 6,260,556 B1 | 7/2001 | Legrand et al. | |
| 6,375,958 B1 | 4/2002 | Cauwet et al. | |
| 6,391,062 B1 * | 5/2002 | Vandenbossche et al. | 8/405 |
| 6,436,151 B1 | 8/2002 | Cottard et al. | |
| 6,436,153 B1 * | 8/2002 | Rondeau | 8/426 |
| 6,475,248 B1 | 11/2002 | Ohashi et al. | |
| 6,570,019 B1 | 5/2003 | Pasquier et al. | |
| 6,592,630 B1 | 7/2003 | Matsunaga et al. | |
| 6,616,709 B1 | 9/2003 | Ohashi et al. | |
| 6,712,861 B1 | 3/2004 | Rondeau | |
| 2001/0010812 A1 | 8/2001 | Chevalier et al. | |
| 2001/0023515 A1 | 9/2001 | Cottard et al. | |
| 2001/0031270 A1 | 10/2001 | Douin et al. | |
| 2001/0034914 A1 | 11/2001 | Saunier et al. | |
| 2001/0054206 A1 * | 12/2001 | Matsunaga et al. | 8/405 |
| 2001/0055580 A1 | 12/2001 | Belli et al. | |
| 2002/0004956 A1 | 1/2002 | Rondeau | |
| 2002/0012681 A1 | 1/2002 | George et al. | 424/401 |
| 2002/0026676 A1 | 3/2002 | Ohashi et al. | |
| 2002/0046432 A1 | 4/2002 | Rondeau | |
| 2002/0088063 A1 | 7/2002 | Ohashi et al. | |
| 2002/0131941 A1 | 9/2002 | Habeck et al. | |
| 2002/0176836 A9 | 11/2002 | Belli et al. | |
| 2002/0176875 A9 | 11/2002 | Douin et al. | |
| 2003/0000023 A9 | 1/2003 | Rondeau | |
| 2003/0019053 A9 | 1/2003 | Rondeau | |
| 2003/0055268 A1 | 3/2003 | Pasquier et al. | |
| 2003/0074747 A1 | 4/2003 | Vuarier et al. | |
| 2003/0124079 A1 | 7/2003 | Mougin et al. | |
| 2003/0131424 A1 | 7/2003 | Audousset et al. | |
| 2004/0019981 A1 | 2/2004 | Cottard et al. | |
| 2004/0034945 A1 | 2/2004 | Javet et al. | |
| 2004/0037796 A1 | 2/2004 | Cottard et al. | |
| 2004/0049860 A1 | 3/2004 | Cottard et al. | |
| 2004/0141943 A1 | 7/2004 | Mougin et al. | |
| 2004/0148711 A1 | 8/2004 | Rondeau | |
| 2004/0205901 A1 | 10/2004 | Cottard et al. | |
| 2004/0258641 A1 | 12/2004 | Plos et al. | |
| 2005/0005368 A1 | 1/2005 | Plos et al. | |
| 2005/0005369 A1 | 1/2005 | Plos et al. | |
| 2005/0008593 A1 | 1/2005 | Plos et al. | |
| 2005/0028301 A1 | 2/2005 | Pastore | |
| 2005/0144741 A1 | 7/2005 | Lang et al. | |

FOREIGN PATENT DOCUMENTS

| | | |
|---|---|---|
| CA | 1255603 | 6/1989 |
| CH | 487 231 | 3/1970 |
| DE | 33 133 32 | 10/1994 |
| DE | 196 46 804 | 5/1997 |
| DE | 196 46 804 A1 | 5/1997 |
| DE | 199 23 438 A1 | 11/2000 |
| DE | 199 26 377 A1 | 12/2000 |
| DE | 100 29 441 A1 | 1/2002 |
| DE | 101 41 683 A1 | 6/2003 |
| DE | 101 48 844 A1 | 10/2003 |
| EP | 0 087 060 B1 | 8/1983 |
| EP | 0 095 238 A2 | 11/1983 |
| EP | 0 080 976 B1 | 9/1986 |
| EP | 0 173 109 | 10/1989 |
| EP | 0 370 470 B1 | 5/1990 |
| EP | 0 412 704 B1 | 2/1991 |
| EP | 0 412 707 B1 | 2/1991 |
| EP | 0 445 342 B1 | 9/1991 |
| EP | 0 486 135 B1 | 5/1992 |
| EP | 0 122 324 B2 | 2/1993 |
| EP | 0 337 354 B1 | 2/1994 |
| EP | 0 582 152 B1 | 2/1994 |
| EP | 0 395 282 | 3/1995 |
| EP | 0 503 853 | 5/1996 |
| EP | 0 714 954 A2 | 6/1996 |
| EP | 0 733 355 A2 | 9/1996 |
| EP | 0 815 828 B1 | 6/1999 |
| EP | 0 970 684 A1 | 1/2000 |
| EP | 1 023 891 B1 | 8/2000 |
| EP | 1 099 437 | 5/2001 |
| EP | 1 132 076 A1 | 9/2001 |
| EP | 1 133 977 A2 | 9/2001 |
| EP | 1 191 041 A2 | 3/2002 |
| EP | 1 464 320 | 10/2004 |
| FR | 1492597 | 9/1966 |
| FR | 1583363 | 10/1969 |
| FR | 2077143 | 10/1971 |
| FR | 2080759 | 11/1971 |
| FR | 2103210 | 7/1972 |
| FR | 2162025 | 7/1973 |
| FR | 2190406 | 2/1974 |
| FR | 2252840 | 6/1975 |
| FR | 2270846 | 12/1975 |
| FR | 2280361 | 2/1976 |
| FR | 2316271 | 1/1977 |
| FR | 2320330 | 3/1977 |
| FR | 2336434 | 7/1977 |
| FR | 2368508 | 5/1978 |
| FR | 2383660 | 10/1978 |
| FR | 2393573 | 1/1979 |
| FR | 2411219 | 7/1979 |
| FR | 2416723 | 9/1979 |
| FR | 2470596 | 6/1981 |
| FR | 2505348 | 11/1982 |
| FR | 2519863 | 7/1983 |
| FR | 2542997 | 9/1984 |

| | | |
|---|---|---|
| FR | 2586913 | 3/1987 |
| FR | 2589476 | 5/1987 |
| FR | 2598611 | 11/1987 |
| FR | 2692572 | 6/1992 |
| FR | 2741261 | 5/1997 |
| FR | 2 773 470 | 7/1999 |
| FR | 2 797 877 | 3/2001 |
| FR | 2800612 | 5/2001 |
| FR | 2811993 | 1/2002 |
| FR | 2820032 | 8/2002 |
| FR | 2830189 | 4/2003 |
| GB | 746864 | 3/1956 |
| GB | 759385 | 10/1956 |
| GB | 1214394 | 1/1970 |
| GB | 1546809 | 5/1979 |
| GB | 1554331 | 10/1979 |
| JP | 48-17362 | 5/1973 |
| JP | 54-86521 | 7/1979 |
| JP | 2-200612 | 8/1990 |
| JP | 6-128128 | 5/1994 |
| JP | 6-183935 | 7/1994 |
| JP | 6-227954 | 8/1994 |
| JP | 8-183716 | 7/1996 |
| JP | 8-208448 | 8/1996 |
| JP | 8-259426 | 10/1996 |
| JP | 9-183714 | 7/1997 |
| JP | 10-23629 | 9/1998 |
| JP | 11-021214 | 1/1999 |
| JP | 11-60453 | 3/1999 |
| JP | 11-343218 | 12/1999 |
| JP | 2000-01417 | 1/2000 |
| JP | 2000-86472 | 3/2000 |
| JP | 2000-505841 | 5/2000 |
| JP | 2001-172120 | 6/2001 |
| JP | 2001-220330 | 8/2001 |
| JP | 2001-226217 | 8/2001 |
| JP | 2001-261534 | 9/2001 |
| JP | 2001-261536 | 9/2001 |
| JP | 2001-294519 | 10/2001 |
| JP | 2001-302473 | 10/2001 |
| JP | 2001-516701 | 10/2001 |
| JP | 2001-516706 | 10/2001 |
| JP | 2001-516707 | 10/2001 |
| JP | 2002-12523 | 1/2002 |
| JP | 2002-12530 | 1/2002 |
| JP | 2002-47151 | 2/2002 |
| JP | 2002-226338 | 8/2002 |
| JP | 2002-249419 | 9/2002 |
| JP | 2001-516705 | 10/2002 |
| JP | 2002-326911 | 11/2002 |
| JP | 2003-55177 | 2/2003 |
| JP | 2004-059468 | 2/2004 |
| JP | 2004-307494 | 11/2004 |
| JP | 2004-307495 | 11/2004 |
| WO | WO 93/11103 | 6/1993 |
| WO | WO 93/23009 | 11/1993 |
| WO | WO 93/23446 | 11/1993 |
| WO | WO 94/02022 | 2/1994 |
| WO | WO 95/00578 | 1/1995 |
| WO | WO 95/01772 | 1/1995 |
| WO | WO 95/15144 | 6/1995 |
| WO | WO 97/18795 | 5/1997 |
| WO | WO 99/12846 | 3/1999 |
| WO | WO 99/13822 | 3/1999 |
| WO | WO 99/13823 | 3/1999 |
| WO | WO 99/13824 | 3/1999 |
| WO | WO 99/13828 | 3/1999 |
| WO | WO 99/13841 | 3/1999 |
| WO | WO 99/13844 | 3/1999 |
| WO | WO 99/13845 | 3/1999 |
| WO | WO 99/13846 | 3/1999 |
| WO | WO 99/13847 | 3/1999 |
| WO | WO 99/13849 | 3/1999 |
| WO | WO 99/20235 A1 | 4/1999 |
| WO | WO 00/68282 | 11/2000 |
| WO | WO 00/71085 A2 | 11/2000 |
| WO | WO 01/43714 A1 | 6/2001 |
| WO | WO 01/62759 A1 | 8/2001 |
| WO | WO 01/78669 | 10/2001 |
| WO | WO 02/32386 A2 | 4/2002 |
| WO | WO 02/38115 A1 | 5/2002 |
| WO | WO 02/39964 A1 | 5/2002 |
| WO | WO 02/45673 A2 | 6/2002 |
| WO | WO 02/58646 A1 | 8/2002 |
| WO | WO 02/58647 A1 | 8/2002 |
| WO | WO 02/74270 | 9/2002 |
| WO | WO 03/22232 A2 | 3/2003 |
| WO | WO 03/28685 A1 | 4/2003 |
| WO | WO 03/029359 | 4/2003 |

OTHER PUBLICATIONS

Co-pending U.S. Appl. No. 10/814,333, filed Apr. 1, 2004.
Co-pending U.S. Appl. No. 10/814,334, filed Apr. 1, 2004.
Co-pending U.S. Appl. No. 10/814,430, filed Apr. 1, 2004.
Co-pending U.S. Appl. No. 10/814,305, filed Apr. 1, 2004.
Co-pending U.S. Appl. No. 10/814,300, filed Apr. 1, 2004.
Co-pending U.S. Appl. No. 10/814,335, filed Apr. 1, 2004.
Co-pending U.S. Appl. No. 10/490,869, filed Apr. 1, 2004.
Co-pending U.S. Appl. No. 10/814,236, filed Apr. 1, 2004.
Co-pending U.S. Appl. No. 10/814,338, filed Apr. 1, 2004.
Co-pending U.S. Appl. No. 10/814,337, filed Apr. 1, 2004.
Co-pending U.S. Appl. No. 10/814,585, filed Apr. 1, 2004.
Co-pending U.S. Appl. No. 10/742,995, filed Apr. 1, 2004.
Co-pending U.S. Appl. No. 10/814,336, filed Apr. 1, 2004.
English Language Derwent Abstract of DE 33 133 32.
English Language Derwent Abstract of DE 100 29 441.
English Language Derwent Abstract of DE 101 41 683.
English Language Derwent Abstract of DE 101 48 844.
English Language Derwent Abstract of DE 199 23 438.
English Language Derwent Abstract of DE 199 26 377.
English Language Derwent Abstract of EP 0 080 976.
English Language Derwent Abstract of EP 0 087 060.
English Language Derwent Abstract of EP 1 023 891.
English Language Derwent Abstract of EP 1 099 437.
English Language Derwent Abstract of FR 2 773 470.
English Language Derwent Abstract of FR 2,797,877.
English Language Derwent Abstract of FR 2,800,612.
English Language Abstract of FR 2 589 476 (EP 0 225 261) from EPO website.
English Language Derwent Abstract of JP 10-23629.
English Language Derwent Abstract of JP 11-060453.
English Language Derwent Abstract of JP 11-21214.
English Language Derwent Abstract of JP 2000-1417.
English Language Derwent Abstract of JP 2000-086472.
English Language Derwent Abstract of JP 2001-172120.
English Language Derwent Abstract of JP 2001-261534.
English Language Derwent Abstract of JP 2001-294519.
English Language Abstract of JP 2001-302473 from EPO website.
English Language Derwent Abstract of JP 2001-516701.
English Language Abstract of JP 2001-516705 from EPO website.
English Language Derwent Abstract of JP 2001-516706.
English Language Derwent Abstract of JP 2001-516707.
English Language Derwent Abstract of JP 2002-226338.
English Language Abstract of JP 2002-249419 from Japio database.
English Language Abstract of JP 2002-326911 from EPO website.
English Language Derwent Abstract of JP 2004-59468.
English Language Derwent Abstract of JP 2-200612.
English Language Derwent Abstract of JP 54-086521.
English Language Derwent Abstract of JP 6-183935.
English Language Derwent Abstract of JP 6-227954.
English Language Derwent Abstract of JP 8-183716.
English Language Derwent Abstact of JP 8-208448.
English Language Derwent Abstact of JP 8-259426.
English Language Abstract of JP 9-183714 from EPO website.

French Search Report for French Patent Application No. FR 02/16669, priority document for Co-pending U.S. Appl. No. 10/742,995, filed Aug. 6, 2003.

French Search Report for French Patent Application No. FR 03/04021, priority document for U.S. Appl. No. 10/814,337, filed Dec. 8, 2003.

French Search Report for French Patent Application No. FR 03/04022, priority document for Co-pending U.S. Appl. No. 10/814,336, filed Nov. 20, 2003.

French Search Report for French Patent Application No. FR 03/04024, priority document for Co-pending U.S. Appl. No. 10/814,585, filed Dec. 8, 2003.

French Search Report for French Patent Application No. FR 03/04026, priority document for Co-pending U.S. Appl. No. 10/814,335, filed Nov. 21, 2003.

French Search Report for French Patent Application No. FR 03/04027, priority document for Co-pending U.S. Appl. No. 10/814,428, filed Nov. 28, 2003.

French Search Report for French Patent Application No. FR 03/04028, priority document for Co-pending U.S. Appl. No. 10/814,236, filed Nov. 25, 2003.

French Search Report for French Patent Application No. FR 03/04029, priority document for Co-pending U.S. Appl. No. 10/814,430, filed Feb. 5, 2004.

French Search Report for French Patent Application No. FR 03/04030, priority document for Co-pending U.S. Appl. No. 10/814,300, filed Nov. 27, 2003.

French Search Report for French Patent Application No. FR 03/04031, priority document for Co-pending U.S. Appl. No. 10/814,333, filed Jan. 8, 2004.

French Search Report for French Patent Application No. FR 03/04033, priority document for Co-pending U.S. Appl. No. 10/814,334, filed Nov. 28, 2003.

French Search Report for French Patent Application No. FR 03/04034, priority document for Co-pending U.S. Appl. No. 10/814,338, filed Feb. 17, 2004.

French Search Report for French Patent Application No. FR 03/04035, priority document for Co-pending U.S. Appl. No. 10/814,305, filed Feb. 5, 2004.

International Search Report for PCT Application No. PCT/FR 02/03252, (for Co-pending U.S. Appl. No. 10/490,869), filed Jan. 20, 2003.

Office Action mailed Nov. 17, 2005 in Co-pending U.S. Appl. No. 10/814,336.

Office Action mailed Nov. 3, 2005 in Co-pending U.S. Appl. No. 10/490,869.

Office Action mailed Nov. 2, 2005 in Co-pending U.S. Appl. No. 10/814,338.

Office Action mailed Nov. 2, 2005 in Co-pending U.S. Appl. No. 10/742,995.

Office Action mailed May 18, 2006 in Co-pending U.S. Appl. No. 10/814,333.

Office Action mailed Jun. 8, 2006 in Co-pending U.S. Appl. No. 10/814,430.

Office Action mailed Mar. 15, 2006 in Co-pending U.S. Appl. No. 10/814,305.

Office Action mailed Mar. 23, 2006 in Co-pending U.S. Appl. No. 10/814,300.

Office Action mailed May 25, 2006 in Co-pending U.S. Appl. No. 10/814,335.

Office Action mailed Mar. 24, 2006 in Co-pending U.S. Appl. No. 10/814,236.

Office Action mailed Mar. 15, 2006 in Co-pending U.S. Appl. No. 10/814,337.

Jacobi, Otto and Jacobi, Gertrud, "Investigation into the reciprocal action of cosmetics and the biosphere of the stratum corneum of the skin," *Cosmetics and Toiletries*, 91:25-32 (Jan. 1976).

Science Des Traitements Capillaires [Hair Treatment Sciences] by Charles Zviak, 1988, published by Masson, pp. 215 and 278.

M. Schlossmann, "The Chemistry and Manufacture of Cosmetics Formulating," 2(3):522-526 (2000).

C. D. Williams et al., "Chemistry and Technology of the Cosmetics and Toiletries Industry," ed. 2, pp. 77-78 (1996).

Yuuki Kagoubutsu Jilen (Dictionary of Organic Compounds), Kodansha Ltd., Aug. 10, 2002, p. 908.

G. Fonnum, J. Bakke and Fk. Hansen—Colloid Polym. Sci. 271:380-389 (1993).

Zviak, C., The Science of Hair Care, pp. 215 and 278 (1986).

* cited by examiner

COMPOSITION FOR DYEING HUMAN KERATIN MATERIALS, COMPRISING AT LEAST ONE FLUORESCENT DYE AND AT LEAST ONE INSOLUBLE POLYORGANOSILOXANE CONDITIONING POLYMER, PROCESS THEREFOR AND USE THEREOF

This application claims benefit of U.S. Provisional Application No. 60/468,079, filed May 6, 2003.

Disclosed herein is a composition comprising at least one fluorescent dye and at least one insoluble polyorganosiloxane conditioning polymer, and also processes and a device for using these compositions. Also disclosed herein is the use of compositions comprising at least one fluorescent dye and at least one insoluble polyorganosiloxane conditioning polymer, for dyeing with a lightening effect human keratin materials, such as keratin fibers, e.g., artificially dyed and/or pigmented hair, and also dark skin.

It is common for individuals with dark skin to wish to lighten their skin and for this purpose to use cosmetic or dermatological compositions containing bleaching agents.

The substances most commonly used as bleaching agents are hydroquinone and its derivatives, kojic acid and its derivatives, azelaic acid, arbutin and its derivatives, alone or in combination with other active agents.

However, these agents are not without their drawbacks. In particular, they may need to be used for a long time and in large amounts in order to obtain a bleaching effect on the skin. No immediate effect is observed on applying compositions comprising them.

In addition, hydroquinone and its derivatives are used in an amount that is effective to produce a visible bleaching effect. In particular, hydroquinone is known for its cytotoxicity towards melanocytes.

Moreover, kojic acid and its derivatives have the drawback of being expensive and consequently of not being able to be used in a large amount in products for commercial mass distribution.

There is thus still a need for cosmetic compositions that may allow a lighter, uniform, homogeneous skin tone of natural appearance to be obtained, wherein these compositions may have satisfactory transparency after application to the skin.

In the field of haircare, there are mainly two major types of hair dyeing.

The first is semi-permanent dyeing, or direct dyeing, which uses dyes capable of giving the hair's natural color a more or less pronounced modification that may withstand shampooing several times. These dyes are known as direct dyes and may be used in two different ways. The colorations may be performed by applying the composition containing the at least one direct dye directly to the keratin fibers, or by applying a mixture, prepared extemporaneously, of a composition containing the at least one direct dye with a composition containing at least one oxidizing bleaching agent, which may be aqueous hydrogen peroxide solution. As used herein, such a process is termed "lightening direct dyeing".

The second is permanent dyeing or oxidation dyeing. This is performed with "oxidation" dye precursors, which may be colorless or weakly colored compounds that, once mixed with oxidizing products, at the time of use, may give rise to colored compounds and dyes via a process of oxidative condensation. It is often necessary to combine one or more direct dyes with the oxidation bases and couplers in order to neutralize or attenuate the shades with too much of a red, orange, or golden glint or, on the contrary, to accentuate these red, orange, or golden glints.

Among the available direct dyes, nitrobenzene direct dyes may not be sufficiently strong, and indoamines, quinone dyes, and natural dyes may have a low affinity for keratin fibers and consequently may lead to colorations that are not sufficiently fast with respect to the various treatments to which the fibers may be subjected, for example with respect to shampooing.

In addition, there is a need to obtain a lightening effect on human keratin fibers. This lightening is conventionally obtained via a process of bleaching the melanins of the hair via an oxidizing system comprising hydrogen peroxide optionally combined with persalts. This bleaching system has the drawback of degrading the keratin fibers and of impairing their cosmetic properties.

Thus, one objective of the present inventors is to solve the problems mentioned above and to propose a composition that has good dyeing affinity for keratin materials, such as keratin fibers, good resistance properties with respect to external agents, for example with respect to shampooing, and that also makes it possible to obtain lightening without impairing the treated material, such as the keratin fibers.

It has thus been found, surprisingly and unexpectedly, that the use of at least one fluorescent dye, such as those in the orange range, in the presence of at least one insoluble polyorganosiloxane conditioning polymer as disclosed herein, may allow these objectives to be achieved.

One embodiment disclosed herein is thus a composition comprising, in a cosmetically acceptable medium, at least one fluorescent dye that is soluble in the medium and at least one conditioning polymer that is insoluble in the medium, wherein the at least one conditioning polymer is chosen from polyorganosiloxanes that do not bear an amine group; the composition not comprising, as the at least one fluorescent agent, 2-[2-(4-dialkylamino)phenylethenyl]-1-alkylpyridinium in which the alkyl radical of the pyridinium nucleus is chosen from methyl and ethyl radicals, the alkyl radical of the benzene nucleus represents a methyl radical, and the counterion is a halide.

Another embodiment concerns a process for dyeing human keratin fibers with a lightening effect, comprising:
   a) applying to the fibers a composition as disclosed herein, for a time that is sufficient to develop a desired coloration and lightening,
   b) optionally rinsing the fibers,
   c) optionally washing the fibers with shampoo and optionally rinsing the fibers, and
   d) drying the fibers or leaving the fibers to dry.

Another embodiment concerns the use of a composition comprising, in a cosmetically acceptable medium, at least one fluorescent dye soluble in the medium, and at least one conditioning polymer insoluble in the medium, wherein the at least one insoluble conditioning polymer is chosen from polyorganosiloxanes that do not bear an amine group, for dyeing human keratin materials with a lightening effect.

Another embodiment is a multi-compartment device for dyeing and/or lightening keratin fibers, comprising at least one compartment containing the composition disclosed herein, and at least one other compartment containing a composition comprising at least one oxidizing agent.

The compositions disclosed herein may allow better fixing of the at least one fluorescent dye onto the keratin materials, which may be reflected by an increased fluorescent effect and a lightening effect that is greater than that obtained with the at least one fluorescent dye used alone.

Better resistance of the result with respect to washing and/or shampooing may also be found.

Other characteristics and advantages of the embodiments disclosed herein will emerge more clearly on reading the description and the example that follows.

As has been mentioned previously, the composition disclosed herein comprises at least one fluorescent dye and at least one insoluble polyorganosiloxane conditioning polymer.

As used herein, the term "fluorescent dye" means a dye which is a molecule that colors by itself, and thus absorbs light in the visible spectrum and possibly in the ultraviolet spectrum (wavelengths ranging from 360 to 760 nanometers), but which, in contrast with a standard dye, converts the absorbed energy into fluorescent light of a longer wavelength emitted in the visible region of the spectrum.

A fluorescent dye as used herein is to be differentiated from an optical brightener. Optical brighteners, which are also known as brighteners, fluorescent brighteners, fluorescent brightening agents, fluorescent whitening agents, whiteners, and fluorescent whiteners, are colorless transparent compounds, which do not dye because they do not absorb light in the visible region, but only in the ultraviolet region (wavelengths ranging from 200 to 400 nanometers), and convert the absorbed energy into fluorescent light of a longer wavelength emitted in the visible region of the spectrum. The color impression is then generated solely by purely fluorescent light that is predominantly blue (wavelengths ranging from 400 to 500 nanometers).

Finally, the fluorescent dye used in the composition is soluble in the medium of the composition. The fluorescent dye differs therein from a fluorescent pigment, which itself is insoluble in the medium of the composition.

The fluorescent dye used in the composition disclosed herein, which is optionally neutralized, is soluble in the medium of the composition to at least 0.001 g/l, for example to at least 0.5 g/l, or for example to at least 1 g/l and, according to one embodiment, to at least 5 g/l at a temperature ranging from 15° C. to 25° C.

Moreover, according to one embodiment described herein, the composition does not comprise, as at least one fluorescent dye, a 2-[2-(4-dialkylamino)phenylethenyl]-1-alkylpyridinium in which the alkyl radical of the pyridinium nucleus is chosen from methyl and ethyl radicals, the alkyl radical of the benzene nucleus represents a methyl radical, and the counterion is a halide.

In accordance with another embodiment, the composition does not comprise, as at least one fluorescent dye, any compounds chosen from azo, azomethine, and methine monocationic heterocyclic fluorescent dyes.

The fluorescent dyes according to certain embodiments are dyes in the orange range.

In certain embodiments, the fluorescent dyes may lead to a reflectance maximum that is in the wavelength range from 500 to 650 nanometers, for example in the wavelength range from 550 to 620 nanometers.

Some of the fluorescent dyes disclosed herein are compounds that are known per se.

As examples of fluorescent dyes that may be used, mention may be made of the fluorescent dyes belonging to the following families: naphthalimides; cationic coumarins; non-cationic coumarins; xanthenodiquinolizines (such as sulphorhodamines); azaxanthenes; naphtholactams; azlactones; oxazines; thiazines; dioxazines; azo, azomethine, and methine polycationic fluorescent dyes, alone or as mixtures; and for example fluorescent dyes belonging to the following families: naphthalimides; cationic coumarins; non-cationic coumarins; azaxanthenes; naphtholactams; azlactones; oxazines; thiazines; dioxazines; azo, azomethine, and methine polycationic fluorescent dyes, alone or as mixtures.

The following may be mentioned among the above dyes:
Brilliant Yellow B6GL sold by the company Sandoz and having the following structure:

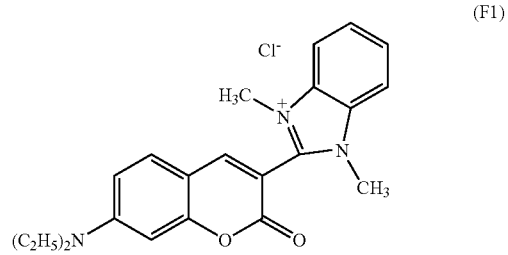

(F1)

Basic Yellow 2, or Auramine O, sold by the companies Prolabo, Aldrich, and Carlo Erba and having the following structure:

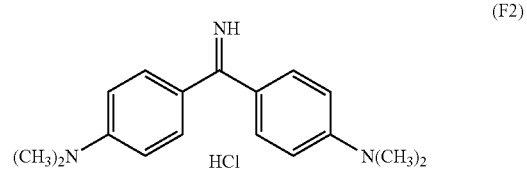

(F2)

4,4'-(imidocarbonyl)bis(N,N-dimethylaniline) monohydrochloride—CAS number 2465-27-2.

Mention may also be made of the compounds having the following formula:

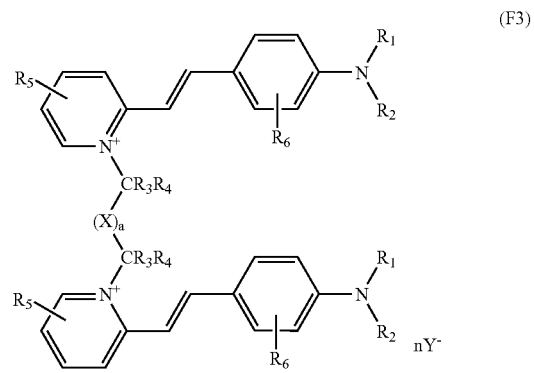

(F3)

in which:
$R_1$ and $R_2$, which may be identical or different, are chosen from:
  hydrogen atoms;
  linear and branched alkyl radicals comprising 1 to 10 carbon atoms, such as from 1 to 4 carbon atoms, wherein said alkyl radicals are optionally interrupted with at least one entity chosen from hetero atoms and groups comprising at least one hetero atom and optionally substituted with with at least one entity chosen from hetero atoms, groups comprising at least one hetero atom, and halogen atoms;

aryl or arylalkyl radicals, the aryl group comprising 6 carbon atoms and the alkyl group comprising 1 to 4 carbon atoms; wherein the aryl group is optionally substituted with at least one linear or branched alkyl radical comprising 1 to 4 carbon atoms, wherein said at least one alkyl radical is optionally interrupted with at least one entity chosen from hetero atoms and groups comprising at least one hetero atom and is optionally substituted with at least one entity chosen from hetero atoms, groups comprising at least one hetero atom, and halogen atoms;

$R_1$ and $R_2$ may optionally be linked so as to form a heterocycle with the nitrogen atom and may comprise at least one other hetero atom, the heterocycle optionally being substituted with at least one linear or branched alkyl radical, wherein said at least one alkyl radical may contain from 1 to 4 carbon atoms and is optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ or $R_2$ may optionally form a heterocycle comprising the nitrogen atom and one of the carbon atoms of the phenyl group bearing the said nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear or branched alkyl radicals comprising 1 to 4 carbon atoms, optionally interrupted with at least one hetero atom;

$R_6$, which may be identical or different, is chosen from hydrogen atoms; halogen atoms; linear or branched alkyl radicals comprising 1 to 4 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:
  linear or branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
  5- or 6-membered heterocyclic radicals optionally substituted with at least one of
    linear or branched alkyl radicals comprising 1 to 14 carbon atoms, optionally substituted with at least one hetero atom;
    linear or branched aminoalkyl radicals comprising 1 to 4 carbon atoms, optionally substituted with at least one hetero atom; and
    halogen atoms;
  fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical being optionally substituted and/or optionally interrupted with at least one entity chosen from hetero atoms and from groups bearing at least one hetero atom;
  dicarbonyl radicals;
  the group X optionally bearing at least one cationic charge;

a being chosen from 0 and 1;

$Y^-$, which may be identical or different, is chosen from organic and mineral anions; and n being an integer at least equal to 2 and at most equal to the number of cationic charges present in the fluorescent dye compound.

As used herein, the term "hetero atoms" means oxygen and nitrogen atoms.

Among the groups bearing such atoms that may be mentioned, inter alia, are hydroxyl, alkoxy, carbonyl, amino, ammonium, amido (—N—CO—), and carboxyl (—O—CO— and —CO—O—) groups.

As regards the alkenyl groups, they may comprise at least one unsaturated carbon-carbon bond (e.g., —C═C—), such as one carbon-carbon double bond.

In the formula (F3), the radicals $R_1$ and $R_2$, which may be identical or different, may be chosen from:
  hydrogen atoms;
  alkyl radicals comprising 1 to 10 carbon atoms, such as 1 to 6 carbon atoms, or such as 1 to 4 carbon atoms, optionally interrupted with an oxygen atom or optionally substituted with at least one radical chosen from hydroxyl, amino, and ammonium radicals, and from chlorine and fluorine atoms;
  benzyl and phenyl radicals optionally substituted with at least one radical chosen from alkyl and alkoxy radicals comprising 1 to 4 carbon atoms, for example 1 or 2 carbon atoms;
  together with the nitrogen atom, heterocyclic radicals chosen from pyrrolo, pyrrolidino, imidazolino, imidazolo, imidazolium, pyrazolino, piperazino, morpholino, morpholo, pyrazolo, and triazoloradicals, optionally substituted with at least one linear or branched alkyl radical comprising 1 to 4 carbon atoms, wherein said at least one alkyl radical is optionally interrupted and/or optionally substituted with at least one of nitrogen atoms, oxygen atoms, groups bearing at least one nitrogen atom, and groups bearing at least one oxygen atom.

As regards the above-mentioned amino and ammonium radicals, the radicals borne by the nitrogen atom may be identical or different and may for example be chosen from hydrogen atoms, $C_1$–$C_{10}$ radicals, such as $C_1$–$C_4$ alkyl radicals, and arylalkyl radicals in which, for example, the aryl group comprises 6 carbon atoms and the alkyl groupl comprises 1 to 10 carbon atoms, such as 1 to 4 carbon atoms.

According to one embodiment disclosed herein, the radicals $R_1$ and $R_2$, which may be identical or different, are chosen from hydrogen atoms; linear and branched $C_1$–$C_6$ alkyl radicals; $C_2$–$C_6$ alkyl radicals substituted with at least one hydroxyl radical; $C_2$–$C_6$ alkyl radicals bearing at least one group chosen from amino and ammonium groups; $C_2$–$C_6$ chloroalkyl radicals; $C_2$–$C_6$ alkyl radicals interrupted with at least one of oxygen atoms and groups bearing an oxygen atom (for example ester); aromatic radicals, for instance phenyl, benzyl, and 4-methylphenyl; heterocyclic radicals such as pyrrolo, pyrrolidino, imidazolo, imidazolino, imidazolium, piperazino, morpholo, morpholino, pyrazolo, and triazolo radicals, optionally substituted with at least one of $C_1$–$C_6$ alkyls and aromatic radicals.

In certain embodiments, the radicals $R_1$ and $R_2$, which may be identical or different, are chosen from hydrogen atoms, linear and branched $C_1$–$C_6$ alkyl radicals such as methyl, ethyl, n-butyl, and n-propyl radicals; 2-hydroxyethyl; alkyltrimethylammonium and alkyltriethylammonium radicals, the alkyl radical being a linear $C_2$–$C_6$ alkyl radical; (di)-alkylmethylamino and (di)alkylethylamino radicals, the alkyl radical being a linear $C_1$–$C_6$ alkyl radical; —$CH_2CH_2Cl$; —$(CH_2)_n$—$OCH_3$ and —$(CH_2)_n$—$OCH_2CH_3$ with n being an integer ranging from 2 to 6; —$CH_2CH_2$—$OCOCH_3$; and —$CH_2CH_2COOCH_3$.

In certain embodiments, the radicals $R_1$ and $R_2$, which may be identical or different, may for example be identical and be chosen from methyl radicals and ethyl radicals.

The radicals $R_1$ and $R_2$, which may be identical or different, may also be chosen from heterocyclic radicals such as pyrrolidino, 3-aminopyrrolidino, 3-(dimethyl)-aminopyrrolidino, 3-(trimethyl)aminopyrrolidino, 2,5-dimethylpyrrolo, 1H-imidazolo, 4-methylpiperazino, 4-benzylpiperazino, morpholo, 3,5-(tert-butyl)-1H-pyrazolo, 1H-pyrazolo, and 1H-1,2,4-triazolo radicals.

The radicals $R_1$ and $R_2$, which may be identical or different, may also be linked so as to form a heterocycle of formulae (I) or (II) below:

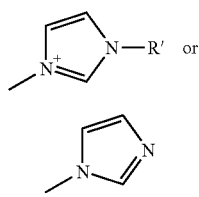

(I)

(II)

in which R' is chosen from a hydrogen atom, $C_1$–$C_3$ alkyl radicals, —$CH_2CH_2OH$, and —$CH_2CH_2OCH_3$.

In accordance with certain embodiments disclosed herein, $R_5$, which may be identical or different, is chosen from hydrogen atoms, fluorine atoms, chlorine atoms, and linear and branched alkyl radicals comprising 1 to 4 carbon atoms optionally interrupted with at least one of oxygen atoms and nitrogen atoms.

It is pointed out that the substituent $R_5$, if it is other than hydrogen, may be in the 3 or 5 position relative to the carbon of the ring bearing the nitrogen substituted with the radicals $R_1$ and $R_2$, for example in position 3 relative to that carbon.

In certain other embodiments, the radicals $R_5$, which may be identical or different, are chosen from hydrogen atoms; linear and branched $C_1$–$C_4$ alkyl radicals; —O—$R_{51}$ where $R_{51}$ is a linear $C_1$–$C_4$ alkyl radical; —$R_{52}$—O—$CH_3$ where $R_{52}$ is a linear $C_2$–$C_3$ alkyl radical; —$R_{53}$—$N(R_{54})_2$ where $R_{53}$ is a linear $C_2$–$C_3$ alkyl radical and $R_{54}$, which may be identical or different, is chosen from hydrogen atoms and methyl radicals.

For example, $R_5$, which may be identical or different, is chosen from hydrogen atoms, methyl radicals, and methoxy radicals, and $R_5$ may be a hydrogen atom.

According to one embodiment, the radicals $R_6$, which may be identical or different, are chosen from hydrogen atoms; linear and branched $C_1$–$C_4$ alkyl radicals; —X wherein X is chosen from chlorine, bromine, and fluorine atoms; —$R_{61}$—O—$R_{62}$ where $R_{61}$ is a linear $C_2$–$C_3$ alkyl radical and $R_{62}$ is a methyl radical; —$R_{63}$—$N(R_{64})_2$ where $R_{63}$ is a linear $C_2$–$C_3$ alkyl radical and $R_{64}$, which may be identical or different, is chosen from hydrogen atoms and methyl radicals; —$N(R_{65})_2$ in which $R_{65}$, which may be identical or different, is chosen from hydrogen atoms and a linear $C_2$–$C_3$ alkyl radical; —$NHCOR_{66}$ where $R_{66}$ is chosen from $C_1$–$C_2$ alkyl radicals, $C_1$–$C_2$ chloroalkyl radicals, radicals —$R_{67}$—$NH_2$, —$R_{67}$—$NH(CH_3)$, —$R_{67}$—$N(CH_3)_2$, —$R_{67}$—$N^+(CH_3)_3$, and —$R_{67}$—$N^+(CH_2CH_3)_3$ where $R_{67}$ is a $C_1$–$C_2$ alkyl radical.

The substituent $R_6$, if it is other than hydrogen, may be in the 2 or 4 position relative to the nitrogen atom of the pyridinium ring, for example in position 4 relative to that nitrogen atom.

In certain embodiments, these radicals $R_6$, which may be identical or different, are chosen from hydrogen atoms, methyl radicals, and ethyl radicals, and $R_6$ for example is a hydrogen atom.

As regards the radicals $R_3$ and $R_4$, these radicals, which may be identical or different, may be chosen from hydrogen atoms and alkyl radicals comprising 1 to 4 carbon atoms, such as methyl radicals. In one example, $R_3$ and $R_4$ are each a hydrogen atom.

As mentioned above, X is chosen from:
linear or branched alkyl radicals comprising 1 to 14 carbon atoms and alkenyl radicals comprising 2 to 14 carbon atoms, wherein said alkyl and alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
5- or 6-membered heterocyclic radicals optionally substituted with at least one of
linear or branched alkyl radicals comprising 1 to 14 carbon atoms;
linear or branched aminoalkyl radicals comprising 1 to 4 carbon atoms, optionally substituted with at least one hetero atom; and
halogen atoms;
fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms wherein said at least one alkyl radical is optionally substituted and/or optionally interrupted with at least one of hetero atoms and groups bearing at least one hetero atom; and
dicarbonyl radicals.

In addition, the group X may bear at least one cationic charge.

Thus, X may be chosen from linear and branched alkyl radicals comprising 1 to 14 carbon atoms and alkenyl radicals comprising 2 to 14 carbon atoms, and may be optionally substituted and/or optionally interrupted with at least one of oxygen and nitrogen atoms, at least one group bearing at least one hetero atom, and fluorine and chlorine atoms.

Among the groups of this type that may be mentioned are hydroxyl, alkoxy (for example, having 1–4 carbons), amino, ammonium, amido, carbonyl, and carboxyl groups (e.g., —COO— and —O—CO—), for example an alkyloxy radical.

The nitrogen atom, if it is present, may be in a quaternized or non-quaternized form. In this case, the other radical or the other two radicals borne by the quaternized or non-quaternized nitrogen atom may be identical or different and may be chosen from hydrogen atoms and $C_1$–$C_4$ alkyl radicals, such as methyl.

According to another embodiment, the group X is chosen from 5- or 6-membered heterocyclic radicals such as imidazolo, pyrazolo, triazino, and pyridino radicals, optionally substituted with at least one of: linear or branched alkyl radicals comprising 1 to 14 carbon atoms, such as 1 to 10 carbon atoms and such as 1 to 4 carbon atoms; linear or branched aminoalkyl radicals comprising 1 to 10 carbon atoms, such as 1 to 4 carbon atoms, optionally substituted with a group comprising at least one hetero atom (for example a hydroxyl radical); and halogen atoms. The amino group may, in one embodiment, be linked to the heterocycle.

In accordance with another embodiment, the group X is chosen from aromatic radicals (for example comprising 6 carbon atoms) and fused or non-fused diaromatic radicals (for example comprising from 10 to 12 carbon atoms), optionally separated with an alkyl radical comprising 1 to 4 carbon atoms, the aromatic or diaromatic radicals optionally being substituted with at least one of halogen atoms and alkyl radicals comprising 1 to 10 carbon atoms, such as 1 to 4 carbon atoms, optionally interrupted with at least one of oxygen atoms, nitrogen atoms, and groups comprising at least one hetero atom (for instance carbonyl, carboxyl, amido, amino, and ammonium radicals).

The aromatic radical, for example a phenyl radical, is linked to the groups $CR_3R_4$ via bonds in positions chosen from 1,2; 1,3; and 1,4, for example in positions 1,3 and 1,4. If the phenyl radical linked via bonds in positions 1,4 bears one or two substituents, this or these substituents may be located in position 1,4 relative to one of the groups $CR_3R_4$. If the phenyl radical linked via bonds in positions 1,3 bears one or two substituents, this or these substituents may be located in at least one of positions 1 and 3 relative to one of the groups $CR_3R_4$.

In the case where the radical is diaromatic, it may be non-fused and comprise two phenyl radicals optionally separated with at least one of single bonds (i.e., a carbon of each of the two rings) and alkyl radicals, such as $CH_2$ and $C(CH_3)_2$ radicals. In one example, the aromatic radicals do not bear a substituent. The diaromatic radical is linked to the groups $CR_3R_4$ via bonds in positions 4,4'.

As examples of groups X that are suitable, mention may be made of linear or branched alkyl radicals comprising 1 to 13 carbon atoms, such as methylene, ethylene, propylene, isopropylene, n-butylene, pentylene, and hexylene; 2-hydroxypropylene and 2-hydroxy-n-butylene; $C_1$–$C_{13}$ alkylene radicals substituted or interrupted with at least one of nitrogen atoms, oxygen atoms, and groups bearing at least one hetero atom (hydroxyl, amino, ammonium, carbonyl and carboxyl radicals, for example), such as —$CH_2CH_2OCH_2CH_2$—, 1,6-dideoxy-d-mannitol, —$CH_2N^+(CH_3)_2CH_2$—, —$CH_2CH_2N^+(CH_3)_2$—$(CH_2)_6N^+$ $(CH_3)_2$—$CH_2CH_2$—, CO—CO—, 3,3-dimethylpentylene, 2-acetoxyethylene, butylene-1,2,3,4-tetraol; —CH═CH—; aromatic or diaromatic radicals substituted with at least one of alkyl radicals, groups bearing at least one hetero atom, and at least one halogen atom, such as 1,4-phenylene, 1,3-phenylene, 1,2-phenylene, 2,6-fluorobenzene, 4,4'-biphenylene, 1,3-(5-methylbenzene), 1,2-bis(2-methoxy)benzene, bis(4-phenyl)methane, methyl 3,4-benzoate, and 1,4-bis(amidomethyl)phenyl; heterocyclic radicals such as pyridine, and derivatives such as the 2,6-bispyridine of imidazole, of imidazolium, and of triazine.

According to one embodiment disclosed herein, X is chosen from linear and branched $C_1$–$C_{13}$ alkyl radicals; —$CH_2CH(OH)CH_2$—; —$CH_2CH(Cl)CH_2$—; —$CH_2CH_2$—$OCOCH_2$—; —$CH_2CH_2COOCH_2$—; —Ra—O—Rb— where Ra is a linear $C_2$–$C_6$ alkyl radical and Rb is a linear $C_1$–$C_2$ alkyl radical;

—Rc—N(Rd)—Re— where Rc is a $C_2$–$C_9$ alkyl radical, Rd is chosen from hydrogen atoms and $C_1$–$C_2$ alkyl radicals and Re is a $C_1$–$C_6$ alkyl radical; —Rf—$N^+(Rg)_2$—Rh— wherein Rf is a linear $C_2$–$C_9$ alkyl radical, Rg, which may be identical, is a $C_1$–$C_2$ alkyl radical and Rh is a linear $C_1$–$C_6$ alkyl radical; and —CO—CO—.

X may furthermore represent an imidazole radical, optionally substituted with at least one alkyl radical comprising 1 to 14 carbon atoms, such as 1 to 10 carbon atoms, or such as 1 to 4 carbon atoms, and for example the divalent radicals having the following formula:

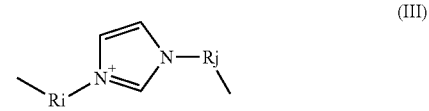

(III)

in which Ri and Rj, which may be identical or different, are chosen from linear $C_1$–$C_6$ alkyl radicals;

X may similarly be chosen from the divalent triazine-based radicals below:

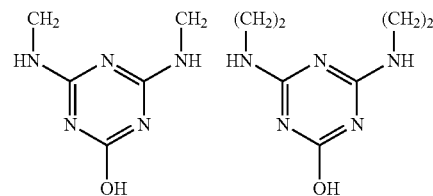

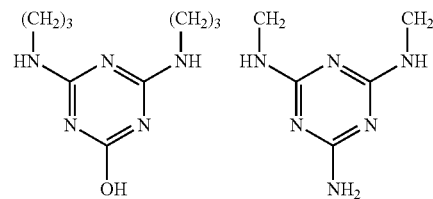

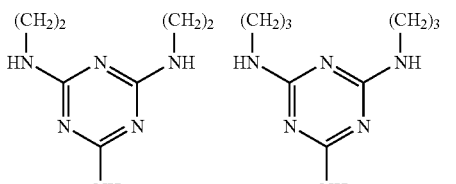

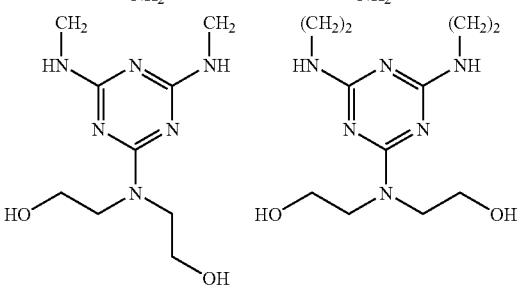

-continued

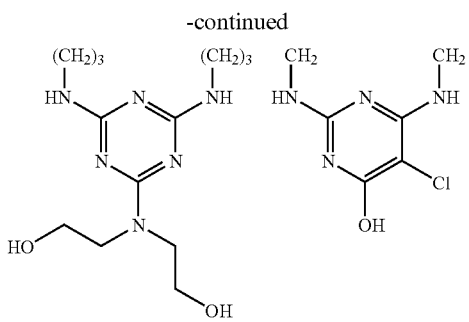

According to another possibility, X may be chosen from the divalent aromatic radicals below:

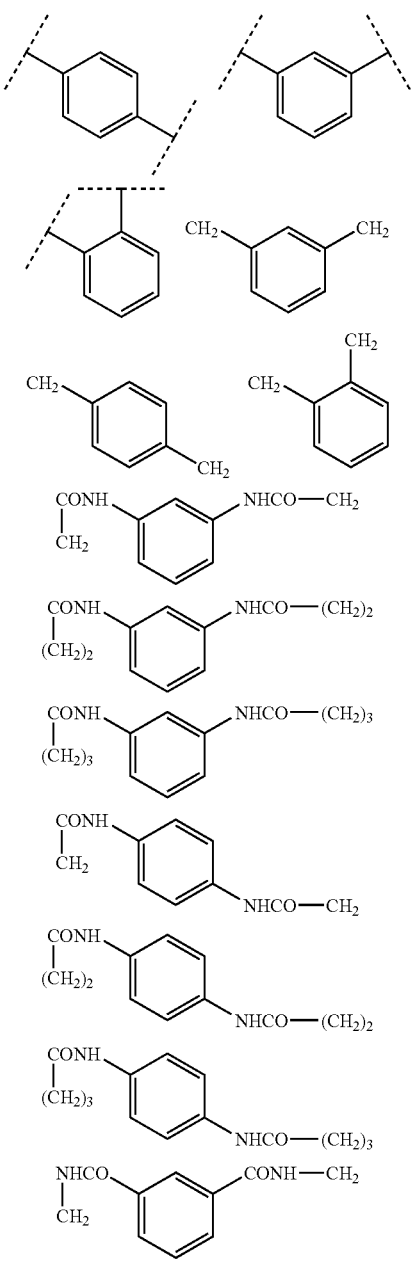

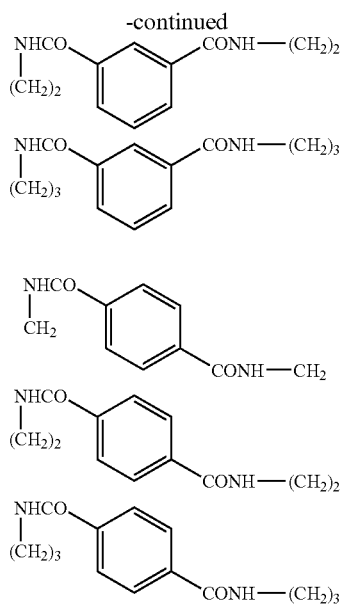

In the general formula of these fluorescent compounds, $Y^-$ is chosen from organic and mineral anions. If there are several anions $Y^-$, these anions may be identical or different.

Among the anions of mineral origin that may be mentioned, without being limited thereto, are anions derived from halogen atoms, such as chlorides, iodides, sulphates, bisulphates, nitrates, phosphates, hydrogen phosphates, dihydrogen phosphates, carbonates, and bicarbonates.

Among the anions of organic origin that may be mentioned are anions derived from the salts of saturated or unsaturated, aromatic or non-aromatic, monocarboxylic or polycarboxylic sulphonic and sulphuric acids, optionally substituted with at least one of hydroxyl and amino radicals, and halogen atoms. Non-limiting examples that are suitable for use include acetates, hydroxyacetates, aminoacetates, (tri)chloroacetates, benzoxyacetates, propionates and derivatives bearing a chlorine atom, fumarates, oxalates, acrylates, malonates, succinates, lactates, tartrates, glycolates, citrates, benzoates and derivatives bearing at least one of methyl and amino radicals, alkyl sulphates, tosylates, benzenesulphonates, and toluenesulphonates, etc.

For example, the anions Y, which may be identical or different, may be chosen from chloride, sulphate, methosulphate, and ethosulphate.

Finally, the integer n is at least equal to 2 and at most equal to the number of cationic charges present in the fluorescent dye compound.

In certain embodiments, the fluorescent dye compounds that have just been described in detail are symmetrical compounds.

These compounds may be synthesized by reacting, in a first step, α-picoline with a reagent comprising two leaving groups that may be chosen from halogen atoms, such as bromine or chlorine, tolylsulphonyl groups, and methanesulphonyl groups.

This first step may take place in the presence of a solvent, for instance dimethylformamide.

The number of moles of α-picoline is generally in the region of 2 per mole of reagent comprising the leaving groups.

In addition, the reaction is usually performed at the reflux temperature of the reagent or of the solvent if a solvent is present.

The product derived from this first step is then placed in contact with a corresponding aldehyde having the following formula:

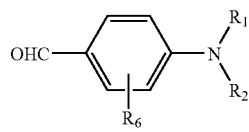

in which $R_1$, $R_2$ and $R_6$ have the same meanings as indicated above.

In this case also, the reaction may be performed in the presence of a suitable solvent, which may be at reflux.

The radicals $R_1$ and $R_2$ of the aldehyde may have the meaning indicated in the general formula detailed previously.

It is also possible to use an aldehyde for which the radicals represent hydrogen atoms and to perform, in accordance with standard methods, the substitution of these hydrogen atoms with suitable radicals as described in the general formula once the second step is complete.

Reference may be made for example to syntheses as described in U.S. Pat. No. 4,256,458, the disclosure of which is hereby incorporated by reference.

The at least one fluorescent dye present in the composition disclosed herein may represent from 0.01% to 20% by weight, such as from 0.05% to 10% by weight, or from 0.1% to 5% by weight, relative to the total weight of the composition.

As mentioned previously, the composition disclosed herein comprises, besides the at least one fluorescent dye, at least one conditioning polymer that is insoluble in the medium of the composition chosen from polyorganosiloxanes which do not bear an amine group.

A conditioning agent may have, for example, the function of improving the cosmetic properties of keratin materials such as the hair, for example the softness, disentangling, feel, smoothness, and static electricity.

In addition, the expression "insoluble in the medium of the composition," as used herein, means any compound which, in all or a part of the concentration ranging from 0.01% to 20% by weight, at room temperature, in the medium of the composition, does not form a macroscopically isotropic transparent solution under these conditions.

In accordance with one embodiment, the insoluble conditioning agents may be in a dispersed form in the medium of the composition in the form of particles generally having a number-average size ranging from 2 nanometers to 100 microns, such as from 30 nanometers to 20 microns (measured with a granulometer).

The insoluble non-amino polyorganosiloxanes (or organosiloxanes or silicones) that are present in the composition may be in the form of oils, waxes, resins, and gums.

The organopolysiloxanes are defined in greater detail in Walter Noll's "Chemistry and Technology of Silicones" (1968) Academic Press. They can be volatile or non-volatile.

When they are volatile, the silicones may be chosen from those having a boiling point ranging from 60° C. to 260° C., and for example may be chosen from:

(i) cyclic silicones comprising from 3 to 7, such as from 4 to 5, silicon atoms. These are, for example, octamethylcyclotetrasiloxane sold under the name Volatile Silicone 7207 by Union Carbide and Silbione 70045 V 2 by Rhodia Chimie, decamethylcyclopentasiloxane sold under the name Volatile Silicone 7158 by Union Carbide, and Silbione 70045 V 5 by Rhodia Chimie, and mixtures thereof.

Mention may also be made of dimethylsiloxane/methylalkylsiloxane cyclocopolymers, such as Volatile Silicone FZ 3109 sold by the company Union Carbide, having the chemical structure:

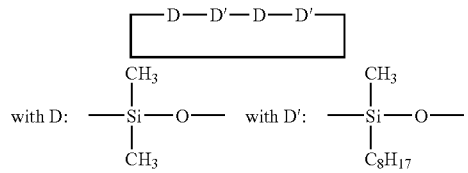

Mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane; and (ii) linear volatile silicones comprising 2 to 9 silicon atoms and having a viscosity of less than or equal to $5 \times 10^{-6}$ m$^2$/s at 25° C. An example is decamethyltetrasiloxane sold under the name SH 200 by the company Toray Silicone. Silicones belonging to this category are also described in the article published in Cosmetics and Toiletries, Vol. 91, January 76, pp. 27–32, Todd & Byers "Volatile Silicone Fluids for Cosmetics".

Non-volatile silicones, such as polyalkylsiloxanes, polyarylsiloxanes, polyalkylarylsiloxanes, silicone gums and resins, polyorganosiloxanes modified with organofunctional groups, and mixtures thereof, may be used. According to one embodiment, polyarylsiloxanes, polyalkylarylsiloxanes, silicone gums and resins, polyorganosiloxanes modified with organofunctional groups, and mixtures thereof, may be used.

These silicones may be chosen from polyalkylsiloxanes, among which mention may be made of polydimethylsiloxanes comprising trimethylsilyl end groups having a viscosity ranging from $5 \times 10^{31\ 6}$ to 2.5 m$^2$/s at 25° C., such as from $1 \times 10^{-5}$ to 1 m$^2$/s. The viscosity of the silicones is measured, for example, at 25° C. according to ASTM standard 445 Appendix C.

Among these polyalkylsiloxanes, mention may be made, in a non-limiting manner, of the following commercial products:

the Silbione® oils of the 47 and 70 047 series and the Mirasil® oils sold by Rhodia Chimie, such as, for example, the oil 70 047 V 500 000;

the oils of the Mirasil series sold by the company Rhodia Chimie;

the oils of the 200 series from the company Dow Corning, such as, DC200 with a viscosity of 60,000 cSt (mm$^2$/s); and the Viscasil® oils from General Electric and certain oils of the SF series (SF 96, SF 18) from General Electric.

Mention may also be made of polydimethylsiloxanes comprising dimethylsilanol end groups (Dimethiconol according to the CTFA name), such as the oils of the 48 series from the company Rhodia Chimie.

In this category of polyalkylsiloxanes, mention may also be made of the products sold under the names Abil® Wax 9800 and 9801 by the company Goldschmidt, which are poly($C_1$–C20)alkylsiloxanes.

The polyalkylarylsiloxanes are chosen from linear or branched polydimethylmethylphenylsiloxanes and polydimethyldiphenylsiloxanes with a viscosity ranging from $1\times10^{-5}$ to $5\times10^{-2}$ m$^2$/s at 25° C.

Among these polyalkylarylsiloxanes, mention may be made, by way of example, of the products sold under the following names:

the Silbione oils of the 70 641 series from Rhodia Chimie;
the oils of the Rhodorsil 70 633 and 763 series from Rhodia Chimie;
the oil Dow Corning 556 Cosmetic Grade Fluid from Dow Corning;
the silicones of the PK series from Bayer, such as the product PK20; and
the silicones of the PN and PH series from Bayer, such as the products PN1000 and PH1000;
certain oils of the SF series from General Electric, such as SF 1023, SF 1154, SF 1250, and SF 1265.

The silicone gums that can be used according to certain embodiments include polydiorganosiloxanes with high number-average molecular masses ranging from 200,000 to 1,000,000, used alone or as a mixture in a solvent. This solvent can be chosen from volatile silicones, polydimethylsiloxane (PDMS) oils, polyphenylmethylsiloxane (PPMS) oils, isoparaffins, polyisobutylenes, methylene chloride, pentane, dodecane, tridecane, and mixtures thereof.

Mention may be made of the following products: polydimethylsiloxane, polydimethylsiloxane/methylvinylsiloxane gums, polydimethylsiloxane/diphenylsiloxane, polydimethylsiloxane/phenylmethylsiloxane, and polydimethylsiloxane/diphenylsiloxane/methylvinylsiloxane.

Products that may also be used in accordance with certain embodiments are mixtures such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;
mixtures formed from a polydimethylsiloxane gum with a cyclic silicone, such as the product SF 1214 Silicone Fluid from the company General Electric. This product is an SF 30 gum corresponding to a dimethicone, having a number-average molecular weight of 500,000, dissolved in the oil SF 1202 Silicone Fluid corresponding to decamethylcyclopentasiloxane;
mixtures of two PDMSs with different viscosities, such as mixtures of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5\times10^{-6}$ m$^2$/s. This product may contain 15% SE 30 gum and 85% SF 96 oil.

The organopolysiloxane resins that can be used according to certain embodiments are crosslinked siloxane systems comprising the following units:

$R_2SiO_{2/2}$, $R_3SiO_{1/2}$, $RSiO_{3/2}$, and $SiO_{4/2}$ in which R is chosen hydrocarbon-based groups comprising 1 to 16 carbon atoms and from phenyl groups. Among these products, those that may be mentioned are the ones in which R denotes a $C_1$–$C_4$ lower alkyl radical, such as a methyl or a phenyl radical.

Among these resins, mention may be made of the product sold under the name Dow Corning 593 and those sold under the names Silicone Fluid SS 4230 and SS 4267 by the company General Electric, which are silicones of dimethyl/trimethyl siloxane structure.

Mention may also be made of the trimethyl siloxysilicate type resins sold for example under the names X22–4914, X21–5034, and X21–5037 by the company Shin-Etsu.

The organomodified silicones that can be used in accordance certain embodiments disclosed herein are silicones as defined above and comprising in their structure at least one organofunctional group attached via a hydrocarbon-based radical. These organofunctional compounds are other than amino groups.

Among the organomodified silicones different from those of formulae (I) or (II), mention may be made of polyorganosiloxanes comprising:

at least one of polyethyleneoxy groups and polypropyleneoxy groups optionally comprising $C_6$–$C_{24}$ alkyl groups, such as the products known as dimethicone copolyol sold by the company Dow Corning under the name DC 1248 and the ($C_{12}$)alkylmethicone copolyol sold by the company Dow Corning under the name Q2 5200;
thiol groups such as the products sold under the names GP 72 A and GP 71 from Genesee;
alkoxylated groups such as the product sold under the name Silicone Copolymer F-755 by SWS Silicones and Abil Wax 2428, 2434, and 2440 by the company Goldschmidt;
hydroxylated groups such as the polyorganosiloxanes comprising a hydroxyalkyl function, described in French Patent Application No. FR A 8516334;
acyloxyalkyl groups such as, for example, the polyorganosiloxanes described in U.S. Pat. No. 4,957,732;
anionic groups of carboxylic type, such as, for example, in the products described in European Patent No. EP 186 507 from the company Chisso Corporation, or of alkylcarboxylic type, such as those present in the product X-22–3701 E from the company Shin-Etsu; 2-hydroxyalkyl sulphonate; and 2-hydroxyalkyl thiosulphate such as the products sold by the company Goldschmidt under the names Abil S201 and Abil S255.

According to certain embodiments, it is also possible to use silicones comprising a polysiloxane portion and a portion comprising a non-silicone organic chain, one of the two portions constituting the main chain of the polymer, the other being grafted onto the said main chain. These polymers are described, for example, in Patent Application Nos. EP A 412 704; EP A 412 707; EP A 640 105; WO 95/00578; EP A 582 152,; and WO 93/23009, and U.S. Pat. Nos. 4,693,935; 4,728,571 and 4,972,037. These polymers may be anionic or nonionic.

Such polymers are, for example, copolymers that can be obtained by free-radical polymerization starting with a monomer mixture comprising:

a) 50% to 90% by weight of tert-butyl acrylate;
b) 0% to 40% by weight of acrylic acid;
c) 5% to 40% by weight of silicone macromer of formula:

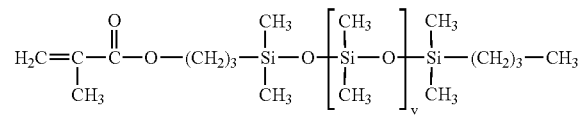

with v being a number ranging from 5 to 700, wherein the weight percentages being calculated relative to the total weight of the monomers.

Other examples of grafted silicone polymers include polydimethylsiloxanes (PDMS) onto which are grafted, via a thiopropylene connecting chain unit, mixed poly(meth) acrylic acid and polyalkyl (meth)acrylate polymer units and polydimethylsiloxanes (PDMS) onto which are grafted, via a thiopropylene connecting chain unit, polyisobutyl (meth) acrylate polymer units.

The silicones can also be used in the form of emulsions, nanoemulsions, and microemulsions.

The silicones that may be mentioned include:

non-volatile silicones chosen from the family of polyalkylsiloxanes comprising trimethylsilyl end groups, such as oils having a viscosity ranging from 0.2 to 2.5 m$^2$/s at 25° C., such as the oils of the DC200 series from Dow Coming, for example that with a viscosity of 60,000 cSt, of the Silbione 70047 and 47 series, for example the oil 70 047 V 500 000, which are sold by the company Rhodia Chimie, polyalkylsiloxanes comprising dimethylsilanol end groups, such as dimethiconols, and polyalkylarylsiloxanes such as the oil Silbione 70641 V 200 sold by the company Rhodia Chimie; and the organopolysiloxane resin sold under the name Dow Corning 593.

The content of insoluble conditioning polymer may range from 0.01% to 20% by weight relative to the total weight of the composition, such as from 0.1% to 10% by weight relative to the total weight of the composition.

The cosmetically acceptable medium may comprise water or a mixture of water and of at least one common organic solvent.

Among the solvents that are suitable for use, mention may be made of alcohols such as ethyl alcohol, isopropyl alcohol, benzyl alcohol and phenylethyl alcohol, glycols and glycol ethers, for instance ethylene glycol monomethyl ether, monoethyl ether and monobutyl ether, propylene glycol and ethers thereof, for instance propylene glycol monomethyl ether, butylene glycol, dipropylene glycol, and diethylene glycol alkyl ethers, for instance diethylene glycol monoethyl ether and monobutyl ether, and alternatively polyols, for instance glycerol. Polyethylene glycols and polypropylene glycols, and mixtures of all these compounds, may also be used as solvent.

The common solvents described above may be present, if present, in an amount ranging from 1% to 40% by weight, for example from 5% to 30% by weight relative to the total weight of the composition.

The pH of the disclosed herein may range from 3 to 12, for example from 5 to 11.

It may be adjusted to the desired value by means of acidifying or basifying agents.

Examples of acidifying agents that may be mentioned include mineral and organic acids, for instance hydrochloric acid, orthophosphoric acid, sulphuric acid, carboxylic acids, for instance acetic acid, tartaric acid, citric acid, and lactic acid, and sulphonic acids.

Examples of basifying agents that may be mentioned include aqueous ammonia, alkaline carbonates, alkanolamines such as monoethanolamine, diethanolamine, triethanolamine, and derivatives thereof, sodium hydroxide, potassium hydroxide, and the compounds of formula (A) below:

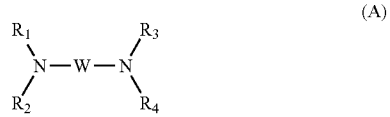

(A)

in which W is a propylene residue optionally substituted with at least one of a hydroxyl group and a $C_1$–$C_6$ alkyl radical; $R_1$, $R_2$, $R_3$ and $R_4$, which may be identical or different, are chosen from hydrogen atoms, $C_1$–$C_6$ alkyl radicals, and $C_1$–$C_6$ hydroxyalkyl radicals.

According to one embodiment, the composition may comprise, in addition to the at least one fluorescent dye, at least one additional non-fluorescent direct dye chosen from nonionic, cationic, and anionic direct dyes, which may be chosen, for example, from nitrobenzene dyes.

The following red and orange nitrobenzene direct dyes may be mentioned:
1-hydroxy-3-nitro-4-N-(γ-hydroxypropyl)aminobenzene,
N-(β-hydroxyethyl)amino-3-nitro-4-aminobenzene,
1-amino-3-methyl-4-N-(β-hydroxyethyl)amino-6-nitrobenzene,
1-hydroxy-3-nitro-4-N-(β-hydroxyethyl)aminobenzene,
1,4-diamino-2-nitrobenzene,
1-amino-2-nitro-4-methylaminobenzene,
N-(β-hydroxyethyl)-2-nitro-para-phenylenediamine,
1-amino-2-nitro-4-(β-hydroxyethyl)amino-5-chlorobenzene,
2-nitro-4-aminodiphenylamine,
1-amino-3-nitro-6-hydroxybenzene,
1-(β-aminoethyl)amino-2-nitro-4-(β-hydroxyethyloxy)benzene,
1-(β,γ-dihydroxypropyl)oxy-3-nitro-4-(β-hydroxyethyl) aminobenzene,
1-hydroxy-3-nitro-4-aminobenzene,
1-hydroxy-2-amino-4,6-dinitrobenzene,
1-methoxy-3-nitro-4-(β-hydroxyethyl)aminobenzene,
2-nitro-4'-hydroxydiphenylamine, and
1-amino-2-nitro-4-hydroxy-5-methylbenzene.

The composition disclosed herein may also comprise, in addition to or instead of these nitrobenzene dyes, at least one additional direct dye chosen from yellow, green-yellow, blue, and violet nitrobenzene dyes, nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, triarylmethane-based dyes, and mixtures thereof.

These additional direct dyes may be basic dyes, among which mention may be made of the dyes known in the Color Index, 3rd edition, under the names "Basic Brown 16", "Basic Brown 17", "Basic Yellow 57", "Basic Red 76", "Basic Violet 10", "Basic Blue 26", and "Basic Blue 99", and acidic direct dyes, among which mention may be made of the dyes known in the Color Index, 3rd edition, under the names "Acid Orange 7", "Acid Orange 24", "Acid Yellow 36", "Acid Red 33", "Acid Red 184", "Acid Black 2", "Acid Violet 43", and "Acid Blue 62", and alternatively cationic direct dyes such as those described in Patent Application Nos. WO 95/01772, WO 95/15144, and EP 714 954, the content of which is incorporated by reference herein.

Among the additional yellow and green-yellow nitrobenzene direct dyes that may be mentioned, for example, are the compounds chosen from:

1-β-hydroxyethyloxy-3-methylamino-4-nitrobenzene,
1-methylamino-2-nitro-5-(β,γ-dihydroxypropyl)oxybenzene,
1-(β-hydroxyethyl)amino-2-methoxy-4-nitrobenzene,
1-(β-aminoethyl)amino-2-nitro-5-methoxybenzene,
1,3-di(β-hydroxyethyl)amino-4-nitro-6-chlorobenzene,
1-amino-2-nitro-6-methylbenzene,
1-(β-hydroxyethyl)amino-2-hydroxy-4-nitrobenzene,
N-(β-hydroxyethyl)-2-nitro-4-trifluoromethylaniline,
4-(β-hydroxyethyl)amino-3-nitrobenzenesulphonic acid,
4-ethylamino-3-nitrobenzoic acid,
4-(β-hydroxyethyl)amino-3-nitrochlorobenzene,
4-(β-hydroxyethyl)amino-3-nitromethylbenzene,
4-(β,γ-dihydroxypropyl)amino-3-nitrotrifluoromethylbenzene,
1-(β-ureidoethyl)amino-4-nitrobenzene,
1,3-diamino-4-nitrobenzene,
1-hydroxy-2-amino-5-nitrobenzene,
1-amino-2-[tris(hydroxymethyl)methyl]amino-5-nitrobenzene,
1-(β-hydroxyethyl)amino-2-nitrobenzene, and
4-(β-hydroxyethyl)amino-3-nitrobenzamide.

Among the additional blue and violet nitrobenzene direct dyes that may be mentioned, for example, are the compounds chosen from:
1-(β-hydroxyethyl)amino-4-N,N-bis(β-hydroxyethyl)amino-2-nitrobenzene,
1-(γ-hydroxypropyl)amino-4,N,N-bis(β-hydroxyethyl)amino-2-nitrobenzene,
1-(β-hydroxyethyl)amino-4-(N-methyl-N-β-hydroxyethyl)amino-2-nitrobenzene,
1-(β-hydroxyethyl),amino-4-(N-ethyl-N-β-hydroxyethyl)amino-2-nitrobenzene,
1-(β,γ-dihydroxypropyl)amino-4-(N-ethyl-N-β-hydroxyethyl)amino-2-nitrobenzene,
2-nitroparaphenylenediamines having the following formula:

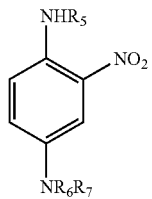

in which:
$R_6$ is chosen from $C_1$–$C_4$ alkyl radicals, β-hydroxyethyl radicals, β-hydroxypropyl radicals, and γ-hydroxypropyl radicals;
$R_5$ and $R_7$, which may be identical or different, are chosen from β-hydroxyethyl, β-hydroxypropyl, γ-hydroxypropyl, and β,γ-dihydroxypropyl radicals, at least one of the radicals $R_6$, $R_7$, and $R_5$ is a γ-hydroxypropyl radical and $R_6$ and $R_7$ are not simultaneously a β-hydroxyethyl radical when $R_5$ is a γ-hydroxypropyl radical, such as those described in French Patent No. FR 2 692 572.

When present, the at least one additional direct dye is present in an amount ranging from 0.0005% to 12% by weight relative to the total weight of the composition, such as from 0.005% to 6% by weight relative to this weight.

When it is intended for oxidation dyeing, the composition disclosed herein may comprise, in addition to the at least one fluorescent dye compound, at least one oxidation base chosen from the oxidation bases conventionally used for oxidation dyeing and among which mention may be made of para-phenylenediamines, bis(phenyl)alkylenediamines, para-aminophenols, ortho-aminophenols, heterocyclic bases, and the acid and alkaline addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4'-aminophenyl-1-(3-hydroxy)pyrrolidine, and the acid and alkaline addition salts thereof.

Among the para-phenylenediamines mentioned above, mention may be made of para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-β-acetylaminoethyloxy-para-phenylenediamine, and the acid and alkaline addition salts thereof.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the acid and alkaline addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and the acid and alkaline addition salts thereof.

Among the ortho-aminophenols that may be mentioned, for example, are 2-aminophenol, 2-amino-5-methylphenol, 2-amino-6-methylphenol, 5-acetamido-2-aminophenol, and the acid and alkaline addition salts thereof.

Among the heterocyclic bases that may be mentioned, for example, are pyridine derivatives, pyrimidine derivatives, pyrazole derivatives, and the acid and alkaline addition salts thereof.

When it is used, the at least one oxidation base may be present in an amount ranging from 0.0005% to 12% by weight relative to the total weight of the composition, such as from 0.005% to 6% by weight relative to this weight.

When it is intended for oxidation dyeing, the composition disclosed herein may also comprise, in addition to the at least one fluorescent dye and the at least one oxidation base, at least one coupler so as to modify and/or to enrich with glints the shades obtained using the at least one fluorescent dye and the at least one oxidation base.

The at least one coupler that may be used in the composition disclosed herein may be chosen from the couplers conventionally used in oxidation dyeing, and among which mention may be made of meta-phenylenediamines, meta-aminophenols, meta-diphenols, heterocyclic couplers, and the acid and alkaline addition salts thereof.

This at least one coupler may be chosen from 2-methyl-5-aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 6-hydroxyindole, 4-hydroxyindole, 4-hydroxy-N-methylindole, 6-hydroxyindoline, 2,6-di-hydroxy-4-methylpyridine, 1H-3-methylpyrazol-5-one, 1-phenyl-3-methylpyrazol-5-one, 2,6-dimethylpyrazolo[1,5-b]-1, 2,4-triazole, 2,6-dimethyl[3,2-c]-1,2,4-triazole, 6-methylpyrazolo[1,5-a]benzimidazole, and the acid and alkaline addition salts thereof.

When present, the at least one coupler may be present in an amount ranging from 0.0001% to 10% by weight, for example from 0.005% to 5% by weight relative to the total weight of the composition.

In general, the acid addition salts that may be used in the context of the compositions disclosed herein (oxidation bases and couplers) may be chosen from hydrochlorides, hydrobromides, sulphates, citrates, succinates, tartrates, tosylates, benzenesulphonates, lactates, and acetates.

The alkaline addition salts that may be used in the context of the compositions disclosed herein (oxidation bases and couplers) may be chosen from the alkali metal addition salts and the alkaline-earth metal addition salts, ammonium addition salts, and organic amine addition salts, including alkanolamines and the compounds of formula (A).

The composition in accordance certain embodiment may also comprise various conventionally used adjuvants, such as anionic, cationic, nonionic, amphoteric, and zwitterionic surfactants and mixtures thereof, anionic, cationic, nonionic, amphoteric, and zwitterionic polymers other than those disclosed herein, and mixtures thereof, mineral thickeners, antioxidants, penetrating agents, sequestering agents, fragrances, buffers, dispersants, conditioners, for instance cations, film-forming agents, ceramides, preserving agents, stabilizers, and opacifiers.

Among the thickeners that may be mentioned are thickening systems based on associative polymers that are well-known to those skilled in the art, such as nonionic, anionic, cationic, andamphoteric associative polymers.

Moreover, when they are present, surfactants, such as nonionic, anionic, and amphoteric surfactants, may be present in an amount ranging from 0.01% to 30% by weight relative to the weight of the composition.

Needless to say, a person skilled in the art will take care to select this or these optional additional compound(s) such that the advantageous properties intrinsically associated with the composition disclosed herein are not, or are not substantially, adversely affected by the envisaged addition(s).

The composition disclosed herein may be in various forms, such as in the form of liquids, shampoos, creams, gels, and in any other suitable form.

In one form that may be mentioned according to certain embodiments, the composition is in the form of a lightening dye shampoo comprising, in a cosmetically acceptable aqueous medium, the composition disclosed herein.

In the composition disclosed herein, when at least one oxidation base is used, optionally in the presence of at least one coupler, or when the at least one fluorescent dye is used in the context of a lightening direct dyeing, then the composition may also comprise at least one oxidizing agent.

The oxidizing agent may be chosen, for example, from hydrogen peroxide, urea peroxide, alkali metal bromates, persalts such as perborates and persulphates, and enzymes such as peroxidases and two-electron and four-electron oxidoreductases. In one embodiment, the oxidizing agent may be chosen from hydrogen peroxide and enzymes.

One embodiment is also the use of a composition comprising, in a cosmetically acceptable medium, at least one soluble fluorescent dye in the medium, at least one insoluble conditioning polymer in the medium, chosen from polyorganosiloxanes which do not bear an amine group, for coloring human keratin materials with a lightening effect.

According to this embodiment, the at least one fluorescent dye may be chosen from fluorescent dyes belonging to the following families: naphthalimides; cationic coumarins; non-cationic coumarins; xanthenodiquinolizines; azaxanthenes; naphtholactams; azlactones; oxazines; thiazines; dioxazines; azo, azomethine, and methane monocationic fluorescent dyes; and azo, azomethine, and methane polycationic fluorescent dyes, alone or as mixtures.

Other compounds that may be mentioned include the compounds of formulae F1, F2 and F3 already detailed previously.

It is similarly possible to use compounds having the following structure (F4):

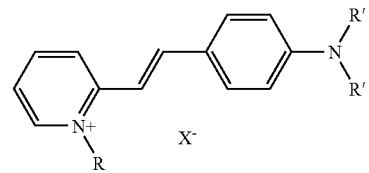

in which formula R is chosen from methyl and ethyl radicals; R' represents a methyl radical, and $X^{31}$ is an anion such as chloride, iodide, sulphate, methosulphate, acetate, or perchlorate.

An example of a compound of this type that may be mentioned is the Photosensitizing Dye NK-557 sold by the company Ubichem, for which R represents an ethyl radical, R' represents a methyl radical, and $X^-$ represents an iodide.

Everything that has been detailed above regarding the nature and amounts of the various ingredients used herein remains valid and will not be repeated in this section of the text.

As used herein, the term "human keratin materials" means the skin, the hair, the nails, the eyelashes, and the eyebrows, for example dark skin and artificially colored and/or pigmented hair.

As used herein, the term "dark skin" means a skin whose lightness L* measured in the CIEL L*a*b* system is less than or equal to 45, for example less than or equal to 40, given that L*=0 is equivalent to black and L*=100 is equivalent to white. The skin types corresponding to this lightness may be African skin, Afro-American skin, Hispano-American skin, Indian skin and North African skin.

As used herein, the expression "artificially dyed and/or pigmented hair" means hair whose tone height is less than or equal to 6 (e.g., dark blond), for example less than or equal to 4 (e.g., chestnut-brown).

The lightening of the hair is evaluated by the "tone height", which characterizes the degree or level of lightening. The notion of "tone" is based on the classification of the natural shades, one tone separating each shade from the shade immediately following or preceding it. This definition and the classification of the natural shades are well-known to hairstyling professionals and are published in the book "Sciences des traitements capillaires [Hair treatment sciences]" by Charles Zviak, 1988, published by Masson, pp. 215 and 278.

The tone heights range from 1 (black) to 10 (light blond), one unit corresponding to one tone; the higher the figure, the lighter the shade.

Another embodiment thus concerns a process for dyeing human keratin fibers with a lightening effect, which comprises:
 a) applying the composition disclosed herein to the keratin fibers, for a time that is sufficient to develop the desired coloration and lightening,
 b) optionally rinsing the fibers,
 c) optionally washing the fibers with shampoo and optionally rinsing, and
 d) drying the fibers or leaving the fibers to dry.

Another embodiment is also a process for coloring dark skin with a lightening effect, in which the composition that has just been described is applied to the skin and the skin is then dried or is left to dry. In certain embodiments, this composition does not comprise any oxidation base or coupler and is not used in the presence of an oxidizing agent.

Everything that has been described above regarding the various constituent components of the composition remains valid, and reference may be made thereto.

The processes disclosed herein are suitable for treating human keratin fibers, such as artificially colored and/or pigmented hair, and alternatively dark skin.

Additionally, the fibers that may be treated with the processes disclosed herein have a tone height of less than or equal to 6 (e.g., dark blond), for example less than or equal to 4 (e.g., chestnut-brown).

Furthermore, a dark skin capable of being treated according to the processes disclosed herein has a lightness L*, measured in the CIEL L*a*b* system, of less than or equal to 45, for example less than or equal to 40.

According to one embodiment, the process of dyeing fibers with a lightening effect is performed with a composition that does not comprise any oxidation dyes or couplers and in the absence of an oxidizing agent.

According to another embodiment, the process of dyeing fibers with a lightening effect is performed with a composition that does not comprise any oxidation dyes or couplers, but in the presence of at least one oxidizing agent.

According to another embodiment of these dyeing processes, at least one composition as defined above is applied to the fibers, such as the hair, for a time that is sufficient to develop a desired coloration and lightening, after which the fibers are rinsed, optionally washed with shampoo, rinsed again, and dried.

According to yet another embodiment of these dyeing processes, at least one composition as defined above is applied to the fibers, such as the hair, without final rinsing.

According to another embodiment, the dyeing process comprises a preliminary step that comprises separately storing, on the one hand, a composition as disclosed herein optionally comprising at least one oxidation base and optionally comprising at least one coupler, and, on the other hand, a composition comprising, in a cosmetically acceptable medium, at least one oxidizing agent, and then in mixing them together at the time of use, after which this mixture is applied to the keratin fibers, such as the hair, for a time that is sufficient to develop the desired coloration, after which the fibers are rinsed, optionally washed with shampoo, rinsed again, and dried.

The time required to develop the coloration and to obtain the lightening effect on the fibers, such as the hair, ranges from about 5 to 60 minutes, for example from about 5 to 40 minutes.

The temperature required to develop the coloration and to obtain the lightening effect may range from room temperature (15° C. to 25° C.) to 80° C., for example from 15° C. and 40° C.

Another embodiment is a multi-compartment device for dyeing keratin fibers, such as the hair, with a lightening effect, comprising at least one compartment containing a composition as disclosed herein, and at least one other compartment containing a composition comprising at least one oxidizing agent. This device may be equipped with a means for applying the desired mixture to the fibers, such as the devices described in French Patent No. FR 2 586 913.

If the composition disclosed herein is used to treat keratin fibers, for example such as chestnut-brown hair, it may achieve the following results:

If the reflectance of the hair is measured when it is irradiated with visible light in the wavelength range from 400 to 700 nanometers, and if the curves of reflectance as a function of the wavelength are compared for hair treated with the composition disclosed herein and untreated hair, it is found that the reflectance curve corresponding to the treated hair, in a wavelength range from 500 to 700 nanometers, is higher than that corresponding to the untreated hair.

This means that, in the wavelength range from 500 to 700 nanometers, such as from 540 to 700 nanometers, there is at least one range in which the reflectance curve corresponding to the treated hair is higher than the reflectance curve corresponding to the untreated hair. As used herein, the term "higher than" means a difference of at least 0.05%, such as at least 0.1%, of reflectance.

However, it is pointed out that there may be, within the wavelength range from 500 to 700 nanometers, such as from 540 to 700 nanometers, at least one range in which the reflectance curve corresponding to the treated fibers is either super-imposable on or lower than the reflectance curve corresponding to the untreated fibers.

In certain embodiments, the wavelength at which the difference is maximal between the reflectance curve for the treated hair and that for the untreated hair is in the wavelength range from 500 to 650 nanometers, such as the wavelength range from 550 to 620 nanometers.

In addition, the composition disclosed herein may be capable of lightening the hair and the skin in a shade which, measured in the CIEL L*a*b* system, has a variable b* of greater than or equal to 6, with a b*/absolute value of a* ratio of greater than 1.2 according to the selection test described below.

Selection Test

The composition is applied to chestnut-brown keratin fibers, such as the hair, at a rate of 10 grams of composition per 1 gram of chestnut-brown fibers. The composition is spread on so as to cover all of the fibers. The composition is left to act for 20 minutes at room temperature (20° C. to 25° C.). The fibers are then rinsed with water and then washed with a lauryl ether sulphate-based shampoo. The fibers are then dried. The spectrocolorimetric characteristics of the fibers are then measured in order to determine the L*a*b* coordinates.

In the CIEL L*a*b* system, a* and b* indicate two color axes: a* indicates the green/red color axis (+a* is red, −a* is green), and b* indicates the blue/yellow color axis (+b* is yellow and −b* is blue); values close to zero for a* and b* correspond to grey shades.

Other than in the operating example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements. The following example is intended to illustrate the invention without limiting the scope as a result.

EXAMPLE

Fluorescent Compound

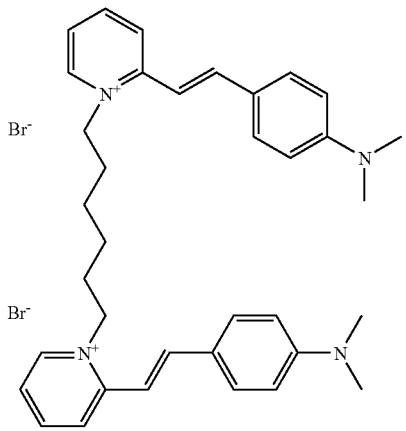

93 g of 2-picoline were reacted with 120 g of 1,6-dibromohexane in dimethylformamide at 110° C. for 5 hours.

The precipitated product was recovered and filtered off.

109 g of the product obtained above were dissolved in methanol, and 82.82 g of p-dimethylaminobenzaldehyde were added in two portions, in the presence of pyrrolidine.

The mixture was then left for 30 minutes.

The product was recovered in precipitated form.

Analysis by mass spectroscopy: 266.

Elemental analysis: C: 62.43%; H: 6.40%; Br: 23.07%; N: 8.09%.

The formula was as follows: $C_{36}H_{44}N_4 \cdot 2Br$.

Compositions

The following composition was prepared (the percentages are expressed by weight of active material):

| | |
|---|---|
| Fluorescent compound | 0.6% |
| Mirasil 70047 V 500000 (Rhodia Chimie) | 0.25% |
| Sodium lauryl ether sulphate (2.2 EO) | 10% |
| Distilled water | qs 100% |

The composition was applied to a lock of chestnut-brown natural hair of tone height 4 with a leave-in time of 20 minutes, a final rinsing operation, and a drying operation under a hood for 30 minutes.

A lock of hair with a marked lightening effect was obtained.

What is claimed is:

1. A composition comprising, in a cosmetically acceptable medium,
(i) at least one fluorescent dye that is soluble in said medium chosen from the following formulae

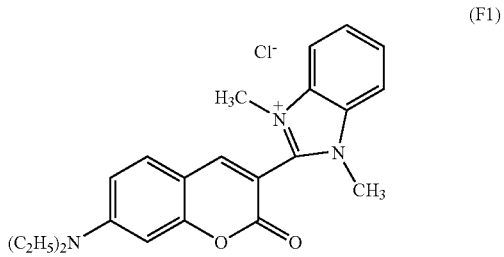

(F1)

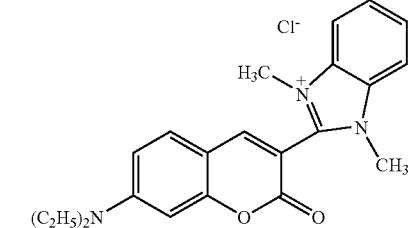

(F3)

in which:

$R_1$ and $R_2$, which may be identical or different, are chosen from:

hydrogen atoms;

linear and branched alkyl radicals comprising 1 to 10 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;

aryl and arylalkyl radicals, the aryl groups comprising 6 carbon atoms and the alkyl groups comprising 1 to 4 carbon atoms; the aryl groups optionally being substituted with at least one linear or branched alkyl radical comprising 1 to 4 carbon atoms and optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ and $R_2$ may optionally be linked so as to form a heterocycle with the nitrogen atom and may comprise at least one other hetero atom, the heterocycle optionally being substituted with at least one linear or branched alkyl radical, optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ or $R_2$ may optionally form a heterocycle comprising the nitrogen atom and one of the carbon atoms of the phenyl group bearing the said nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear and branched alkyl radicals comprising 1 to 4 carbon atoms, optionally interrupted with at least one hetero atom;

$R_6$, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:
linear and branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;

5- or 6-membered heterocyclic radicals optionally substituted with at least one of
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;

fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical optionally substituted and/or optionally interrupted with at least one entity chosen from hetero atoms and groups bearing at least one hetero atom;

dicarbonyl radicals;

the group X optionally bearing at least one cationic charge;

a is chosen from 0 and 1;

$Y^-$, which may be identical or different, is chosen from organic and mineral anions; and n is an integer at least equal to 2 and at most equal to the number of cationic charges present in the at least one fluorescent dye, and (ii) at least one conditioning polymer that is insoluble in said medium, wherein the at least one conditioning polymer is chosen from polyorganosiloxanes which do not bear an amine group.

2. A composition according to claim 1, wherein the at least one fluorescent dye provides a reflectance maximum that is in the wavelength range from 500 to 650 nanometers.

3. A composition according to claim 2, wherein the at least one fluorescent dye leads to a reflectance maximum that is in the wavelength range from 550 to 620 nanometers.

4. A composition according to claim 1, wherein $R_1$ and $R_2$, which may be identical or different, are chosen from linear or branched alkyl radicals comprising 1 to 4 carbon atoms.

5. A composition according to claim 1, wherein $R_1$ and $R_2$, which may be identical or different, are linked so as to form a heterocycle with the nitrogen atom and comprise at least one other hetero atom, the heterocycle being substituted with at least one linear or branched alkyl radical comprising 1 to 4 carbon atoms.

6. A composition according to claim 1, wherein the at least one fluorescent dye is present in an amount ranging from 0.01% to 20% by weight relative to the total weight of the composition.

7. A composition according to claim 6, wherein the at least one fluorescent dye is present in an amount ranging from 0.05% to 10% by weight relative to the total weight of the composition.

8. A composition according to claim 7, wherein the at least one fluorescent dye is present in an amount ranging from 0.1% to 5% by weight relative to the total weight of the composition.

9. A composition according to claim 1, wherein the at least one insoluble conditioning polymer is chosen from silicones in the form of oils, waxes, resins, and gums.

10. A composition according to claim 9, wherein the silicones are chosen from cyclic volatile silicones comprising from 3 to 7 silicon atoms, cyclocopolymers, linear volatile silicones comprising from 2 to 9 silicon atoms, non-volatile polyalkylsiloxane, polyarylsiloxane, polyalkylarylsiloxane and polyorganosiloxane silicones modified with organofunctional groups, grafted silicones comprising a polysiloxane portion and a portion comprising a non-silicone organic chain, and polydiorganosiloxane, organopolysiloxane and trimethylsiloxysilicate resins, and mixtures thereof.

11. A composition according to claim 10, wherein the organofunctional groups are chosen from polyethyleneoxy and polypropyleneoxy groups optionally comprising alkyl groups, thiol groups, alkoxylated groups, hydroxylated groups, acyloxyalkyl groups, and carboxylic, sulphonate, and thiosulphate anionic groups.

12. A composition according to claim 1, wherein the at least one insoluble conditioning polymer is present in an amount ranging from 0.01% to 20% by weight relative to the total weight of the composition.

13. A composition according to claim 12, wherein the at least one insoluble conditioning polymer is present in an amount ranging from 0.1% to 10% by weight relative to the total weight of the composition.

14. A composition according to claim 1, further comprising at least one surfactant chosen from nonionic, anionic, and amphoteric surfactants.

15. A composition according to claim 14, wherein the surfactant is present in an amount ranging from 0.01% to 30% by weight relative to the total weight of the composition.

16. A composition according to claim 1, further comprising at least one non-fluorescent additional direct dye chosen from nonionic, cationic, and anionic direct dyes.

17. A composition according to claim 16, wherein the at least one non-fluorescent additional direct dye is chosen from nitrobenzene dyes, azo dyes, anthraquinone dyes, naphthoquinone dyes, benzoquinone dyes, phenothiazine dyes, indigoid dyes, xanthene dyes, phenanthridine dyes, phthalocyanin dyes, and triarylmethane-based dyes.

18. A composition according to claim 16, wherein the at least one non-fluorescent additional direct dye is present in an amount ranging from 0.0005% to 12% by weight relative to the total weight of the composition.

19. A composition according to claim 18, wherein the at least one non-fluorescent additional direct dye is present in an amount ranging from 0.005% to 6% by weight relative to the total weight of the composition.

20. A composition according to claim 1, wherein the composition is in the form of a lightening dyeing shampoo.

21. A composition according to claim 1, further comprising at least one oxidation base chosen from para-phenylenediamines, bis(phenyl)alkylenediamines, para-aminophenols, ortho-aminophenols, heterocyclic bases, and the acid and alkaline addition salts thereof.

22. A composition according to claim 21, wherein the at least one oxidation base is present in an amount ranging from 0.0005% to 12% by weight relative to the total weight of the composition.

23. A composition according to claim 22, wherein the at least one oxidation base is present in an amount ranging from 0.005% to 6% by weight relative to the total weight of the composition.

24. A composition according to claim 21, further comprising at least one coupler chosen from meta-phenylenediamines, meta-aminophenols, meta-diphenols, heterocyclic couplers, and the acid and alkaline addition salts thereof.

25. A composition according to claim 24, wherein the at least one coupler is present in an amount ranging from 0.0001% to 10% by weight relative to the total weight of the composition.

26. A composition according to claim 25, wherein the at least one coupler is present in an amount ranging from 0.005% to 5% by weight relative to the total weight of the composition.

27. A composition according to claim 1, further comprising at least one oxidizing agent.

28. A composition according to claim 27, wherein the at least one oxidizing agent is chosen from hydrogen peroxide, urea peroxide, alkali metal bromates, persalts, and enzymes.

29. A composition according to claim 28, wherein the persalts are chosen from perborates and persulphates.

30. A composition according to claim 28, wherein the enzymes are chosen from peroxidases, two electron oxidoreductases, and four electron oxidoreductases.

31. A composition according to claim 28, wherein the at least one oxidizing agent is hydrogen peroxide.

32. A composition according to claim 1, wherein the at least one fluorescent dye compound is a dye in the orange range.

33. A process for dyeing human keratin fibers with a lightening effect, comprising;
a) applying a dye composition comprising, in a cosmetically acceptable medium,
(i) at least one fluorescent dye that is soluble in said medium chosen from the following formulae

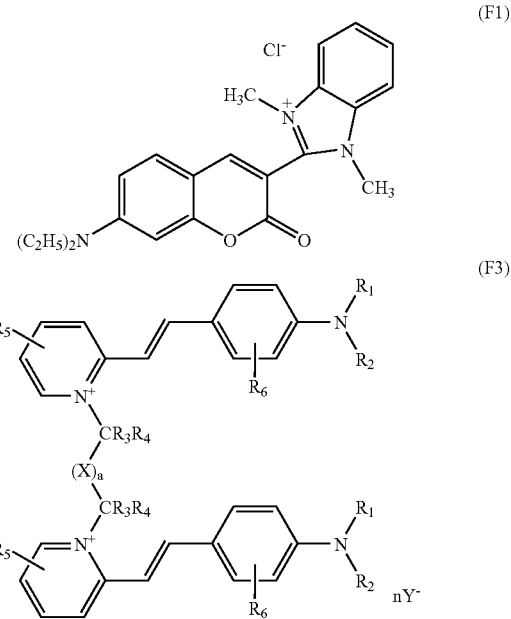

in which;
$R_1$ and $R_2$, which may be identical or different, are chosen from:
hydrogen atoms;
linear and branched alkyl radicals comprising 1 to 10 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, the aryl groups comprising 6 carbon atoms and the alkyl groups comprising 1 to 4 carbon atoms; the aryl groups optionally being substituted with at least one linear or branched alkyl radical comprising 1 to 4 carbon atoms and optionally interrupted with at least one entity chosen from hetero atoms and groups comprising at least one hetero atom and optionally substituted with at least one entity chosen from hetero atoms, groups comprising at least one hetero atom, and halogen atoms;
$R_1$ and $R_2$ may optionally be linked so as to form a heterocycle with the nitrogen atom and may comprise at least one other hetero atom, the heterocycle optionally being substituted with at least one linear or branched alkyl radical, optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ or $R_2$ may optionally form a heterocycle comprising the nitrogen atom and one of the carbon atoms of the phenyl group bearing the said nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear and branched alkyl radicals comprising 1 to 4 carbon atoms, optionally interrupted with at least one hetero atom;

$R_6$, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:
linear and branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;

5- or 6-membered heterocyclic radicals optionally substituted with at least one of
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;

fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical optionally substituted and/or optionally interrupted with at least one entity chosen from hetero atoms and groups bearing at least one hetero atom;
dicarbonyl radicals;
the group X optionally bearing at least one cationic charge;

a is chosen from 0 and 1;

$Y^-$, which may be identical or different, is chosen from organic and mineral anions; and n is an integer at least equal to 2 and at most equal to the number of cationic charges present in the at least one fluorescent dye, and (ii) at least one conditioning polymer that is insoluble in said medium, wherein the at least one conditioning polymer is chosen from polyorganosiloxanes which do not bear an amine group;

and wherein the composition does not comprise, as the at least one fluorescent dye, 2-[2-(4-dialkylamino)phenylethenyl]-1-alkylpyridinium in which the alkyl radical of the pyridinium nucleus is chosen from methyl and ethyl radicals, the alkyl radical of the benzene nucleus represents a methyl radical, and a counterion is a halide to the said fibers, for a time that is sufficient to develop a desired coloration and lightening;

b) optionally rinsing the fibers;
c) optionally washing the fibers with shampoo and optionally rinsing the fibers; and
d) drying the fibers or leaving the fibers to dry.

34. A process for dyeing human keratin fibers with a lightening effect comprising
a) separately storing,
(i) a dye composition comprising, in a cosmetically acceptable medium,
(a) at least one fluorescent dye that is soluble in said medium chosen from the following formulae

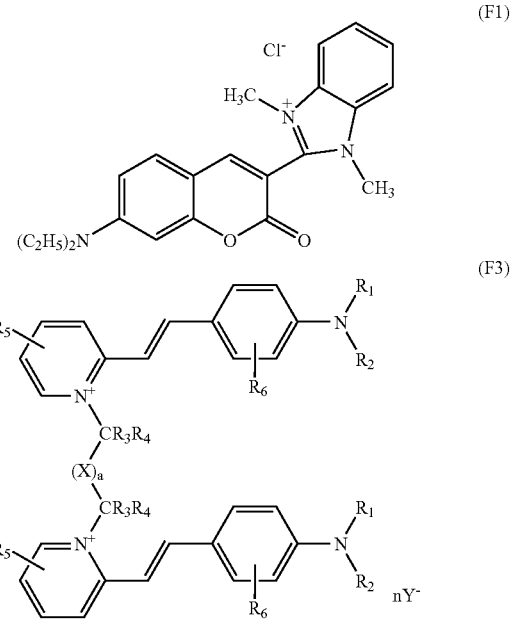

in which;

$R_1$ and $R_2$, which may be identical or different, are chosen from:
hydrogen atoms;
linear and branched alkyl radicals comprising 1 to 10 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, the aryl groups comprising 6 carbon atoms and the alkyl groups comprising 1 to 4 carbon atoms; the aryl groups optionally being substituted with at least one linear or branched alkyl radical comprising 1 to 4 carbon atoms and optionally interrupted with at least one entity chosen from hetero atoms and groups comprising at least one hetero atom and optionally substituted with at least one entity chosen from hetero atoms, groups comprising at least one hetero atom, and halogen atom;

$R_1$ and $R_2$ may optionally be linked so as to form a heterocycle with the nitrogen atom and may comprise at least one other hetero atom, the heterocycle optionally being substituted with at least one linear or branched alkyl radical, optionally interrupted with at least one entity chosen from hetero atoms and groups comprising at least one hetero atom and optionally substituted with at least one entity chosen from hetero atoms, groups comprising at least one hetero atom, and halogen atoms;

$R_1$ or $R_2$ may optionally form a heterocycle comprising the nitrogen atom and one of the carbon atoms of the phenyl group bearing the said nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear and branched alkyl radicals comprising 1 to 4 carbon atoms, optionally interrupted with at least one hetero atom;

$R_6$, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:

linear and branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen 5- or 6-membered heterocyclic radicals optionally substituted with at least one of linear or branched alkyl radicals comprising 1 to 14 carbon atoms, optionally substituted with at least one hetero atom;

linear or branched aminoalkyl radicals comprising 1 to 4 carbon atoms, optionally substituted with at least one hetero atom; and halogen atoms;

fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical optionally substituted and/or optionally interrupted with at least one entity chosen from hetero atoms and groups bearing at least one hetero atom;

dicarbonyl radicals;

the group X optionally bearing at least one cationic charge; a is chosen from 0 and 1;

$Y^-$, which may be identical or different, is chosen from organic and mineral anions; and n is an integer at least equal to 2 and at most equal to the number of cationic charges present in the at least one fluorescent dye, and (b) least one conditioning polymer that is insoluble in said medium, wherein the at least one conditioning polymer is chosen from polyorganosiloxanes which do not bear an amine group;

and wherein the composition does not comprise, as the at least one fluorescent dye, 2-[2-(4-dialkylamino) phenylethenyl]-1-alkylpyridinium in which the alkyl radical of the pyridinium nucleus is chosen from methyl and ethyl radicals, the alkyl radical of the benzene nucleus represents a methyl radical, and a counterion is a halide (ii) a composition comprising, in a cosmetically acceptable medium, at least one oxidizing agent, b) mixing (i) and (ii) together at the time of use, c) applying this mixture to the fibers for a time that is sufficient to develop a desired coloration, d) optionally rinsing said fibers e) optionally washing said fibers with shampoo and optionally rinsing said fibers, and f) drying said fibers or leaving said fibers to dry.

35. A process according to claim 33, wherein the composition is applied to hair with a tone height of less than or equal to 6.

36. A process according to claim 35, wherein the composition is applied to hair with a tone height of less than or equal to 4.

37. A process according to claim 33, wherein the human keratin fibers are artificially colored and/or pigmented.

38. A process for coloring dark skin with a lightening effect, comprising applying to the skin a composition comprising, in a cosmetically acceptable medium, (i) at least one fluorescent dye that is soluble in said medium chosen from the following formulae

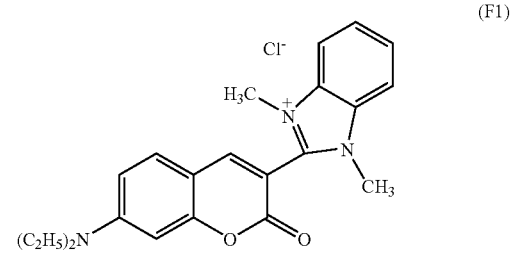

(F1)

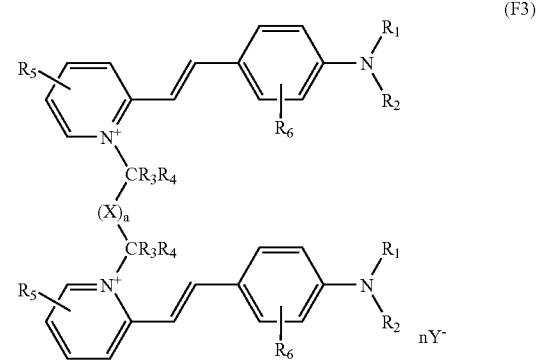

(F3)

in which;

$R_1$ and $R_2$, which may be identical or different, are chosen from:

hydrogen atoms;
linear and branched alkyl radicals comprising 1 to 10 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
aryl and arylalkyl radicals, the aryl groups comprising 6 carbon atoms and the alkyl groups comprising 1 to 4 carbon atoms; the aryl groups optionally being substituted with at least one linear or branched alkyl radical comprising 1 to 4 carbon atoms and optionally interrupted with at least one entity chosen from hetero atoms and groups comprising at least one hetero atom and optionally substituted with at least one entity chosen from hetero atoms, groups comprising at least one hetero atom, and halogen atoms;
$R_1$ and $R_2$ may optionally be linked so as to form a heterocycle with the nitrogen atom and may comprise at least one other hetero atom, the heterocycle optionally being substituted with at least one linear or branched alkyl radical, optionally interrupted with at least one entity chosen from hetero atoms and groups comprising at least one hetero atom and optionally substituted with at least one entity chosen from hetero atoms, groups comprising at least one hetero atom, and halogen atoms;
$R_1$ or $R_2$ may optionally form a heterocycle comprising the nitrogen atom and one of the carbon atoms of the phenyl group bearing the said nitrogen atom;
$R_3$ and $R_4$, which may be identical or different, are chosen from hydrogen atoms and alkyl radicals comprising 1 to 4 carbon atoms;
$R_5$, which may be identical or different, is chosen from hydrogen atoms, halogen atoms, and linear and branched alkyl radicals comprising 1 to 4 carbon atoms, optionally interrupted with at least one hetero atom;
$R_6$, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;
X is chosen from:
linear and branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
5- or 6-membered heterocyclic radicals optionally substituted with at least one of
linear or branched alkyl radicals comprising 1 to 14 carbon atoms, optionally substituted with at least one hetero atom;
linear or branched aminoalkyl radicals comprising 1 to 4 carbon atoms, optionally substituted with at least one hetero atom; and
halogen atoms;
fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical optionally substituted and/or optionally interrupted with at least one entity chosen from hetero atoms and groups bearing at least one hetero atom;
dicarbonyl radicals;
the group X optionally bearing at least one cationic charge;
a is chosen from 0 and 1;
$Y^-$, which may be identical or different, is chosen from organic and mineral anions; and
n is an integer at least equal to 2 and at most equal to the number of cationic charges present in the at least one fluorescent dye, and
(ii) at least one conditioning polymer that is insoluble in said medium, wherein the at least one conditioning polymer is chosen from polyorganosiloxanes which do not bear an amine group;
and wherein the composition does not comprise, as the at least one fluorescent dye, 2-[2-(4-dialkylamino)phenylethenyl]-1-alkylpyridinium in which the alkyl radical of the pyridinium nucleus is chosen from methyl and ethyl radicals, the alkyl radical of the benzene nucleus represents a methyl radical, and a counterion is a halide; and
drying the skin or leaving the skin to dry.
39. A multi-compartment device for dyeing and/or lightening keratin fibers, comprising
at least one compartment containing a composition comprising, in a cosmetically acceptable medium,
(i) at least one fluorescent dye that is soluble in said medium chosen from the following formulae

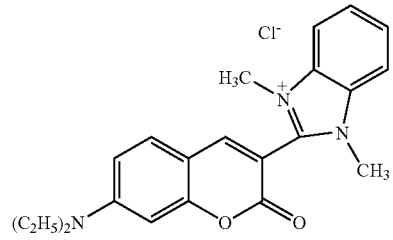

(F1)

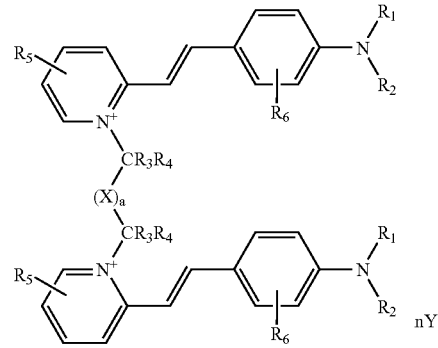

(F3)

in which;

R₁ and R₂, which may be identical or different, are chosen from:
  hydrogen atoms;
  linear and branched alkyl radicals comprising 1 to 10 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
  aryl and arylalkyl radicals, the aryl groups comprising 6 carbon atoms and the alkyl groups comprising 1 to 4 carbon atoms; the aryl groups optionally being substituted with at least one linear or branched alkyl radical comprising 1 to 4 carbon atoms and optionally interrupted with at least one entity chosen from hetero atoms and groups comprising at least one hetero atom and optionally substituted with at least one entity chosen from hetero atoms, groups comprising at least one hetero atom, and halogen atoms;
  R₁ and R₂ may optionally be linked so as to form a heterocycle with the nitrogen atom and may comprise at least one other hetero atom, the heterocycle optionally being substituted with at least one linear or branched alkyl radical, optionally interrupted with at least one entity chosen from hetero atoms and groups comprising at least one hetero atom and optionally substituted with at least one entity chosen from hetero atoms, groups comprising at least one hetero atom, and halogen atoms;
  R₁ or R₂, may optionally form a heterocycle comprising the nitrogen atom and one of the carbon atoms of the phenyl group bearing the said nitrogen atoms;

R₃ and R₄, which may be identical or different, are chosen from hydrogen atoms and alkyl radicals comprising 1 to 4 carbon atoms;

R₅, which may be identical or different, is chosen from hydrogen atoms, halogen atoms, and linear and branched alkyl radicals comprising 1 to 4 carbon atoms, optionally interrupted with at least one hetero atom;

R₆, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:
  linear and branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
  5- or 6-membered heterocyclic radicals optionally substituted with at least one of
    linear or branched alkyl radicals comprising 1 to 14 carbon atoms, optionally substituted with at least one hetero atom;
    linear or branched aminoalkyl radicals comprising 1 to 4 carbon atoms, optionally substituted with at least one hetero atom; and
    halogen atoms;
  fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical optionally substituted and/or optionally interrupted with at least one entity chosen from hetero atoms and groups bearing at least one hetero atom;
  dicarbonyl radicals;
  the group X optionally bearing at least one cationic charge;

a is chosen from 0 and 1;

Y⁻, which may be identical or different, is chosen from organic and mineral anions; and n is an integer at least equal to 2 and at most equal to the number of cationic charges present in the at least one fluorescent dye, and (ii) at least one conditioning polymer that is insoluble in said medium, wherein the at least one conditioning polymer is chosen from polyorganosiloxanes which do not bear an amine group;

and wherein the composition does not comprise, as the at least one fluorescent dye, 2-[2-(4-dialkylamino) phenylethenyl]-1-alkylpyridinium in which the alkyl radical of the pyridinium nucleus is chosen from methyl and ethyl radicals, the alkyl radical of the benzene nucleus represents a methyl radical, and a counterion is a halide; and at least one other compartment containing a composition comprising at least one oxidizing agent.

40. A process for dyeing keratin materials with a lightening effect comprising applying to keratin materials a dye composition comprising, in a cosmetically acceptable medium,
  (i) at least one fluorescent dye that is soluble in the said medium chosen from the following formulae

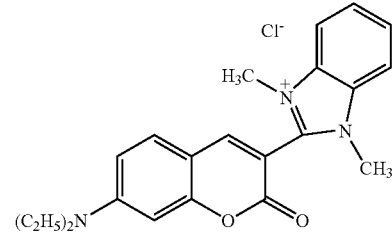

(F1)

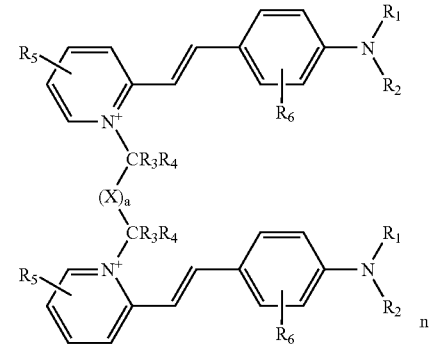

(F3)

in which;

$R_1$ and $R_2$, which may be identical or different, are chosen from:
- hydrogen atoms;
- linear and branched alkyl radicals comprising 1 to 10 carbon atoms, wherein said alkyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
- aryl and arylalkyl radicals, the aryl groups comprising 6 carbon atoms and the alkyl groups comprising 1 to 4 carbon atoms; the aryl groups optionally being substituted with at least one linear or branched alkyl radical comprising 1 to 4 carbon atoms and optionally interrupted with at least one entity chosen from hetero atoms and groups comprising at least one hetero atom and optionally substituted with at least one entity chosen from hetero atoms, groups comprising at least one hetero atom, and halogen
- $R_1$ and $R_2$ may optionally be linked so as to form a heterocycle with the nitrogen atom and may comprise at least one other hetero atom, the heterocycle optionally being substituted with at least one linear or branched alkyl radical, optionally interrupted with at least one entity chosen from hetero atoms and groups comprising at least one hetero atom and optionally substituted with at least one entity chosen from hetero atoms, groups comprising at least one hetero atom, and halogen atoms;
- $R_1$ or $R_2$ may optionally form a heterocycle comprising the nitrogen atom and one of the carbon atoms of the phenyl group bearing the said nitrogen atom;

$R_3$ and $R_4$, which may be identical or different, are chosen from hydrogen atoms and alkyl radicals comprising 1 to 4 carbon atoms;

$R_5$, which may be identical or different, is chosen from hydrogen atoms, halogen atoms, and linear and branched alkyl radicals comprising 1 to 4 carbon atoms, optionally interrupted with at least one hetero atom;

$R_6$, which may be identical or different, is chosen from hydrogen atoms; halogen atoms; linear and branched alkyl radicals comprising 1 to 4 carbon atoms, optionally interrupted with at least one entity chosen from hetero atoms and groups comprising at least one hetero atom and optionally substituted with at least one entity chosen from hetero atoms, groups comprising at least one hetero atom, and halogen atoms;

X is chosen from:
- linear and branched alkyl radicals comprising 1 to 14 carbon atoms and alkenyl radicals comprising 2 to 14 carbon atoms, wherein said alkyl radicals and said alkenyl radicals are optionally interrupted with at least one entity chosen from hetero atoms and groups comprising at least one hetero atom and optionally substituted with at least one entity chosen from hetero atoms, groups comprising at least one hetero atom, and halogen atoms;
- 5- or 6-membered heterocyclic radicals optionally substituted with at least one of
  - linear or branched alkyl radicals comprising 1 to 14 carbon atoms, optionally interrupted with at least one hetero atom;
  - linear or branched aminoalkyl radicals comprising 1 to 4 carbon atoms, optionally substituted with at least one hetero atom; and
  - halogen atoms;
- fused or non-fused aromatic or diaromatic radicals, optionally separated with an alkyl radical comprising 1 to 4 carbon atoms, the aromatic or diaromatic radicals optionally being substituted with at least one halogen atom or with at least one alkyl radical comprising 1 to 10 carbon atoms, said at least one alkyl radical optionally substituted and/or optionally interrupted with at least one entity chosen from hetero atoms and groups bearing at least one hetero atom;
- dicarbonyl radicals;
- the group X optionally bearing at least one cationic charge;

a is chosen from 0 and 1;

$Y^-$, which may be identical or different, is chosen from organic and mineral anions; and n is an integer at least equal to 2 and at most equal to the number of cationic charges present in the at least one fluorescent dye, and (ii) at least one conditioning polymer that is insoluble in the said medium, said at least one conditioning polymer being chosen from polyorganosiloxanes not bearing an amino group.

41. A process according to claim 40, wherein the at least one fluorescent dye gives a reflectance maximum that is in the wavelength range from 500 to 650 nanometers.

42. A process according to claim 41, wherein the at least one fluorescent dye gives a reflectance maximum that is in the wavelength range from 550 to 618 nanometers.

43. A process according to claim 40, wherein the at least one fluorescent dye is chosen from fluorescent compounds belonging to the following families; naphthalimides; cationic coumarins; non-cationic coumarins; xanthenodiquinolizines; azaxanthenes; naphtholactams; azlactones; oxazines; thiazines; dioxazines; azo, azomethine, and methine type monocationic fluorescent dyes; azo, azomethine, and methine type polycationic fluorescent dyes; and mixtures thereof.

44. A process according to claim 40, wherein

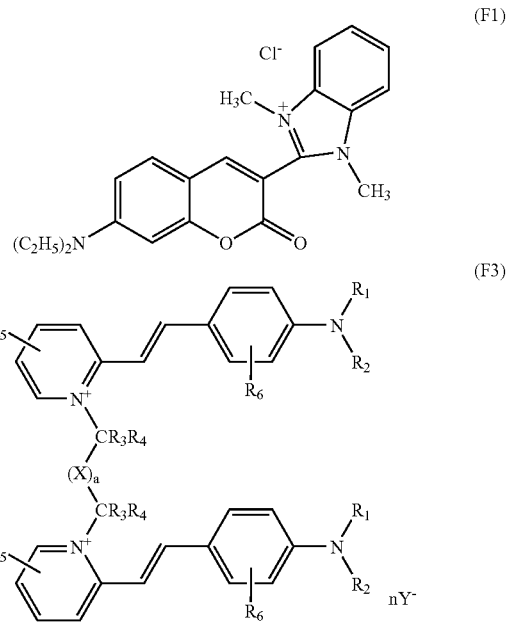

n is an integer at least equal to 2 and at most equal to the number of cationic charges present in the at least one fluorescent dye:

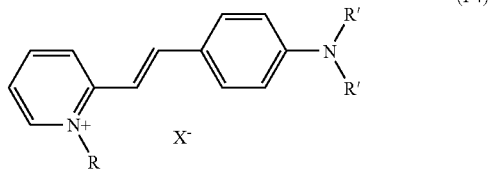

in which formula R is chosen from methyl and ethyl radicals; R' is a methyl radical and X⁻ is an anion.

45. A process according to claim 40, wherein $R_1$ and $R_2$, which may be identical or different, are chosen from linear and branched alkyl radicals comprising 1 to 4 carbon atoms.

46. A process according to claim 40, wherein $R_1$ and $R_2$, which may be identical or different, are linked so as to form a heterocycle with the nitrogen atom and comprise at least one other hetero atom, the heterocycle being substituted with at least one linear or branched alkyl radical comprising 1 to 4 carbon atoms.

47. A process according to claim 44, wherein X is an anion chosen from chloride, iodide, sulphate, methasulphate, acetate, and perchlorate.

48. A process according to claim 41, wherein the keratin materials are artificially colored and/or pigmented keratin fibers.

49. A process according to claim 48, wherein the keratin material is hair.

50. A process according to claim 48, wherein the keratin material is dark skin.

51. A process according to claim 49, wherein the hair has a tone height of less than or equal to 6.

52. A method according to claim 51, wherein the hair has a tone height of less than or equal to 4.

* * * * *

UNITED STATES PATENT AND TRADEMARK OFFICE
CERTIFICATE OF CORRECTION

PATENT NO. : 7,147,673 B2
APPLICATION NO. : 10/814334
DATED : December 12, 2006
INVENTOR(S) : Grégory Plos and Henri Samain It is certified that error appears in the above-identified patent and that said Letters Patent is hereby corrected as shown below:

On the title page, item (57), line 9, "tightening" should read --lightening--.

In claim 33, column 30, line 12, "comprising;" should read --comprising:--.

In claim 33, column 30, line 44, "which;" should read --which:--.

In claim 34, column 32, line 49, "which;" should read --which:--

In claim 34, column 33, line 42, after "halogen" insert --atoms;--.

In claim 34, column 34, line 4, "(b) least" should read --(b)     at least--.

In claim 38, column 34, line 65, "which;" should read --which:--.

In claim 38, column 36, lines 27-28, "2-[2-(4-dialkylamino) phenylethenyl]-1 -alkylpyridinium" should read --2-[2-(4-dialkylamino)phenylethenyl]-1-alkylpyridinium--.

In claim 39, column 37, line 1, "which;" should read --which:--.

In claim 39, column 37, line 31, "$R_2$, may" should read --$R_2$ may--.

In claim 39, column 38, lines 26-27, "2-[2-(4-dialkylamino) phenylethenyl]-1 -alkylpyridinium" should read --2-[2-(4-dialkylamino)phenylethenyl]-1-alkylpyridinium--.

In claim 40, column 39, line 1, "which;" should read --which:--.

In claim 40, column 39, line 20, after "halogen" insert --atoms;--.

In claim 43, column 40, line 33, "families;" should read --families:--.

UNITED STATES PATENT AND TRADEMARK OFFICE
CERTIFICATE OF CORRECTION

PATENT NO.        : 7,147,673 B2
APPLICATION NO. : 10/814334
DATED             : December 12, 2006
INVENTOR(S)       : Grégory Plos and Henri Samain It is certified that error appears in the above-identified patent and that said Letters Patent is hereby corrected as shown below:

In claim 47, column 42, line 5, "X" should read --$X^-$--.

Signed and Sealed this

Sixth Day of March, 2007

JON W. DUDAS
*Director of the United States Patent and Trademark Office*